United States Patent
De Souza et al.

(10) Patent No.: US 9,073,904 B2
(45) Date of Patent: Jul. 7, 2015

(54) PREPARATION OF POSACONAZOLE INTERMEDIATES

(75) Inventors: Dominic De Souza, Holzkirchen (DE);
Shreerang V. Joshi, Navi Mumbai (IN);
Sachin Bhuta, Navi Mumbai (IN);
Abhinay C. Pise, Navi Mumbai (IN);
Dattatraya N. Chavan, Navi Mumbai (IN); Shashikant D. Metkar, Navi Mumbai (IN)

(73) Assignee: SANDOZ AG, Basel (CH)

( * ) Notice: Subject to any disclaimer, the term of this patent is extended or adjusted under 35 U.S.C. 154(b) by 45 days.

(21) Appl. No.: 13/697,802

(22) PCT Filed: May 18, 2011

(86) PCT No.: PCT/EP2011/058036
§ 371 (c)(1),
(2), (4) Date: Mar. 27, 2013

(87) PCT Pub. No.: WO2011/144656
PCT Pub. Date: Nov. 24, 2011

(65) Prior Publication Data
US 2013/0203994 A1    Aug. 8, 2013

(30) Foreign Application Priority Data
May 19, 2010    (EP) ...................................... 10163215

(51) Int. Cl.
*C07D 249/08*    (2006.01)
*C07D 405/14*    (2006.01)
*C07D 405/06*    (2006.01)

(52) U.S. Cl.
CPC ............ *C07D 405/14* (2013.01); *C07D 249/08* (2013.01); *C07D 405/06* (2013.01)

(58) Field of Classification Search
USPC ...................................................... 548/268.8
See application file for complete search history.

(56) References Cited

U.S. PATENT DOCUMENTS

| | | | |
|---|---|---|---|
| 4,957,730 A | 9/1990 | Bohn et al. | |
| 5,403,937 A | 4/1995 | Saksena et al. | |
| 5,595,872 A | 1/1997 | Wetterau et al. | |
| 5,693,626 A | 12/1997 | Saksena et al. | |
| 5,710,154 A | 1/1998 | Saksena et al. | |
| 5,714,490 A | 2/1998 | Saksena et al. | |
| 5,834,472 A | 11/1998 | Sangekar et al. | |
| 5,972,381 A | 10/1999 | Sangekar et al. | |
| 6,355,801 B1 | 3/2002 | Giesinger et al. | |
| 6,958,337 B2 | 10/2005 | Andrews et al. | |
| 2010/0197621 A1 | 8/2010 | Henry et al. | |

FOREIGN PATENT DOCUMENTS

| | | |
|---|---|---|
| EP | 0736030 | 10/1996 |
| EP | 1230231 | 8/2002 |
| EP | 01394162 | 3/2004 |
| WO | 9309114 | 5/1993 |
| WO | 9425452 A1 | 11/1994 |
| WO | 9516658 A1 | 6/1995 |
| WO | 9517407 A1 | 6/1995 |
| WO | 9633163 | 10/1996 |
| WO | 9633178 | 10/1996 |
| WO | 9638443 | 12/1996 |
| WO | 9700255 A1 | 1/1997 |
| WO | 9722579 | 6/1997 |
| WO | 9722710 A1 | 6/1997 |
| WO | 9733178 | 9/1997 |
| WO | 9918097 | 4/1999 |
| WO | 02080678 | 10/2002 |
| WO | 2005/075473 | 8/2005 |
| WO | 2005117831 | 12/2005 |
| WO | 2006007540 | 1/2006 |
| WO | 2007/122156 | 11/2007 |
| WO | 2007/143390 | 12/2007 |
| WO | 2008/136279 | 11/2008 |
| WO | 2009/058267 | 5/2009 |
| WO | 2009/129297 | 10/2009 |
| WO | 2009/141837 | 11/2009 |
| WO | 2010000668 | 1/2010 |
| WO | 2011/144653 | 11/2011 |
| WO | 2011/144655 | 11/2011 |
| WO | 2011/144657 | 11/2011 |
| WO | 2013/186320 | 12/2013 |

OTHER PUBLICATIONS

Blundell et al., Synlett 1994, pp. 263-265.
Brown et al., J. Chem. Soc. 2003, 125 (36), 10808-10809.
Cordova et al., Chem. Eur. J. 2004, 10 (15), 3673-3684.
Hayashi et al., J. Org. Chem. 2005, 69 (18), 5966-5973.
Hepperle et al., Tetrahedron Lett. 2002, 43, 3359-3363.

(Continued)

*Primary Examiner* — Rebecca Anderson
*Assistant Examiner* — Karen Cheng
(74) *Attorney, Agent, or Firm* — Jeffrey S. Melcher; Manelli Selter PLLC

(57) ABSTRACT

The present invention relates to process for the preparation of a chiral compound of formula (IX) or a salt thereof, wherein $Y_1$ and $Y_2$ are independently F or Cl, preferably F, the crystalline compound of formula (IX) as such, and its use for the preparation of an antifungal agent.

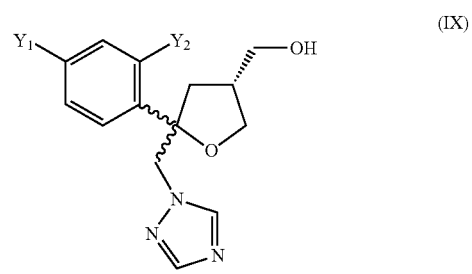

4 Claims, 5 Drawing Sheets

(56) References Cited

OTHER PUBLICATIONS

Peterson, "Carbonyl olefination reaction using silyl-substituted organometallic compounds", J. Org. Chem (1968) 33 (2) pp. 780-784.
Saksena et al., Tetrahedron Lett. 2004, 45 (44), 8249-8251.
Weicheng Thou et al., Survey of Syntheses of Azole Antifungals. Chinese Journal of Pharmaceuticals, vol. 37, No. 2, pp. 125-133, Dec. 31, 2006.
Sixi Wang, Synthesis of SIPI-4678 and Voriconazole, The Master Degree Theses of the Shanghai Institute of Parmaceutical Industry, pp. 10-13, Mar. 2007.
Sixi, Wang, Synthesis of SIPI-4678 and Voriconazole, The Master Degree Theses of the Shanghai Institute of Pharmaceutical Industry, pp. 9-17, Jan. 24, 2007.
Chinese Office Action issued in Application No. 201180024340.2, Mar. 24, 2014, pp. 1-13, and translation.
Chinese Office Action issued in Application No. 201180024363.3, Jan. 17, 2014, pp. 1-7, and translation.
Chinese Office Action issued in Application No. 201180024632.6, May 20, 2014, pp. 1-10, and translation.
Robert V. Hoffman, Organic Chemistry: An Intermediate Text, Second Edition, John Wiley & Sons, Inc., 2004, p. 128.
Serajuddin, Abu. Advanced Drug Delivery Reviews 59 (2007) pp. 603-616.
Reichardt, Chr. Solvents and Solvent Effects in Organic Chemistry. 3rd ed. Wiley-VCH. (2004) pp. 418-421.
Parmee, "Human beta3 adreneergic receptor containing cyclic ureidobenzenesulonafides," Bioorganic & Medicinal Chemistry Letters, vol. 9, 1999, pp. 749-745, XP002648199.
International Preliminary Report on Patentability issued in PCT/EP2012/061346, WO2012/172015, Oct. 9, 2013, pp. 1-8.
International Search Report issued in PCT/EP2012/061346, WO2012/172015, Aug. 1, 2012, pp. 1-9.
Written Opinion issued in PCT/EP2012/061346, WO2012/172015, Jun. 20, 2013, pp. 1-5.
International Preliminary Report on Patentability issued in PCT/EP2012/061346, WO2012/172015, Jun. 3, 1014, pp. 1-29.
International Search Report issued in PCT/EP2013/062298, WO2013/186320, Feb. 8, 2013, pp. 1-4.
Written Opinion issued in PCT/EP2013/062298,WO2013/186320, Feb. 8, 2013, pp. 1-13.
Di Santo et al., "Antifungal estrogen-like imidazoles. Synthesis and antifungal activities of thienyl and 1H-pyrrolyl derivatives of 1-aryl-2-(1H-imidazol-1-yl)ethane", European Journal of Medicinal Chemistry, Editions Scientifique Elsevier, Paris, FR, vol. 32, No. 2, Jan. 1, 1997, pp. 143-149.

Greene et al., Protective Groups in Organic Synthesis:, 2nd ed., John Wiley & Sons, New York 1991 10-142.
Greene et al., Protective Groups in Organic Synthesis:, 3rd ed., Wiley-Interscience (1999).
Huang et al., Organic Letters 2004, 6 (25) 4795-4798.
Kurome et al., "Total Synthesis of an Antifungal Cyclic Depsipeptide Aureobasidin A", Tetrahedron, Elsevier Science Publishers. Amsterdam, NL, vol. 52, No. 12. Mar. 18, 1996, pp. 4327-4346.
Na Y-M et al., "Synthesis and antifungal activity of new 1-halogenbenzyl-3-imidazoly 1methylindole derivatives", European Journal of Medicinal Chemistry, Editions Scientifique Elsevier, Paris, FR, vol. 38, No. 1, Jan. 1, 2003, pp. 75-87.
Remington's Pharmaceutical Sciences, 15th Ed., Mack Publishing Co., New Jersey (1991).
Tetrahedron Letters 32 (1991). pp. 7545-7548.
Xianhai Huang et al., "Manipulation of N,O-Nucleophilicity: Efficient Formation of 4-N-Substituted 2,4-Dihydro-3H-1, 2, 4-Triazolin-3-ones", Organic Letters, American Chemical Society, US, vol. 6, No. 25, Nov. 10, 2004, pp. 4795-4798.
International Search Report and Written Opinion Mailed Sep. 9, 2011 in PCT/EP2011/058035.
International Search Report and Written Opinion Mailed Aug. 4, 2011 in PCT/EP2011/058036.
International Search Report and Written Opinion Mailed Aug. 5, 2011 in PCT/EP2011/058039.
International Search Report and Written Opinion Mailed Jul. 13, 2011 in PCT/EP2011/058033.
Hacker, "Aromatic 2-(Thio)ureidocarboxylic Acids as New Family of Modulators of Multidrug Resistance-Associated Protein 1: Synthesis, Biological Evaluation, and Structure-Activity Relationships," Journal of Medicinal Chemistry, 2009, vol. 52, No. 15, pp. 4587-4593.
Office Action issued in Chinese Patent Application No. 2011800243402, Dec. 8, 2014, pp. 1-13, translation included.
Saksena, Anil K.; Girijavallabhan, Viyyoor M.; Lovey, Raymond G.; Pike, Russell E.; Wang, Haiyan; Ganguly, Ashit K.; Morgan, Brian; Zaks, Alesey; Puar, Mohinder S., Highly stereoselective access to novel 2,2,4-trisubstituted tetrahydrofurans by halocyclization: practical chemoenzymic synthesis of SCH 51048, a broad-spectrum orally active antifungal agent, Tetrahedron Letters, 1995, 36(11), pp. 1787-1790.
Konosu, Toshiyuki; Tajima, Yawara; Miyaoka, Takeo; Oida, Sadao, Concise synthesis of optically active oxirane precursors for the preparation of triazole antifungals using the Friedel-Crafts reaction of (S)-2-tosyloxypropionyl chloride, Tetrahedron Letters, 1991, 32(51), pp. 7545-7548.
The Chemical Society of Japan, Handbook of Chemistry, Applied Chemistry 6th Ed., Maruzen, Jan. 30, 2003, p. 178.
Japanese Office Action issued Mar. 3, 2015, in Japanese Patent Application No. 2013-510614, pp. 1-6.

PREPARATION OF POSACONAZOLE INTERMEDIATES

The present invention relates to the preparation of chiral compounds, in particular to the preparation of chiral compounds which may be used as intermediates for the preparation of antifungal agents, preferably posaconazole.

BACKGROUND PRIOR ART

Posaconazole (CAS Registry Number 171228-49-2; CAS Name: 2,5-anhydro-1,3,4-trideoxy-2-C-(2,4-difluorophenyl)-4-[[4-[4-[4-[1-[(1S,2S)-1-ethyl-2-hydroxypropyl]-1,5-dihydro-5-oxo-4H-1,2,4-triazol-4-yl]phenyl]-1-piperazinyl]phenoxy]methyl]-1-(1H-1,2,4-triazol-1-yl)-D-threo-pentitol) is a triazole antifungal drug represented by the structure:

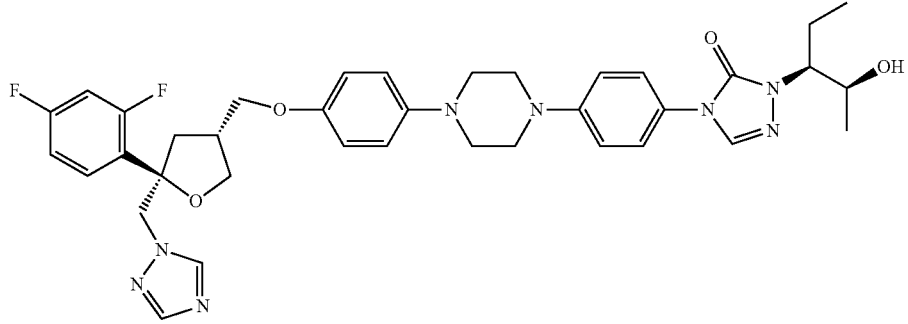 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

Posaconazole is used, for example, to prevent and/or treat invasive fungal infections caused by *Candida* species, *Mucor* species, *Aspergillus* species, *Fusarium* species, or *Coccidioides* species in immunocompromised patients and/or in patients where the disease is refractory to other antifungal agents such as amphothericin B, fluconazole, or itraconazole, and/or in patients who do not tolerate these antifungal agents.

One of the important intermediates for the preparation of posaconazole is the compound of formula (IX)

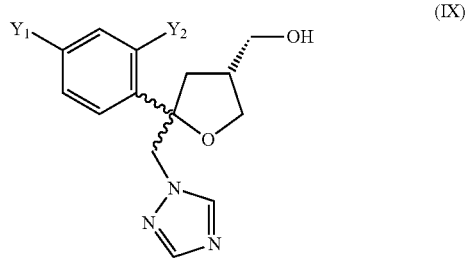

(IX)

wherein both residues $Y_1$ and $Y_2$ are F. Therefore, there generally is a constant need for advantageous processes for the preparation of this intermediate.

According to the known prior art processes, a common starting material for the preparation of chiral compounds according to formula (IX) is a substituted olefin compound according to the following formula (II)

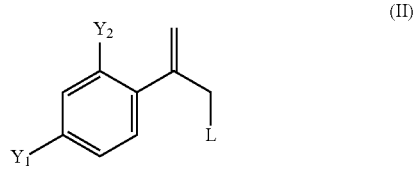

(II)

wherein L is a suitable leaving group such Cl, Br, and sulfonates.

However, said prior art processes provide only comparatively complicated processes for the preparation of these compounds of formula (II), abbreviated in the following by Ar—C(=CH$_2$)—CH$_2$-L, in particular compounds wherein $Y_1$ and $Y_2$ are both F.

WO 94/25452 discloses a process wherein a Ar—C(=CH$_2$)—CH$_2$-L is obtained by reacting the respective allylic alcohol Ar—C(=CH$_2$)—CH$_2$—OH with either a brominating agent or a sulfonylating agent. In order to obtain the allylic alcohol in turn, several procedures are taught in the literature.

One procedure described in WO 94/25452 starts from Ar—C(=O)—CH$_2$-L from which, in a 3-step process, the allylic alcohol is obtained. In the first step, Ar—C(=O)—CH$_2$—Cl is reacted with KOAc (potassium acetate) to obtain Ar—C(=O)—CH$_2$—OAc which is then subjected to a reaction with CH$_3$Ph$_3$PBr (methyltriphenylphosphonium bromide) and NaHMDS (sodium hexamethyldisilazane) in the presence of THF (tetrahydrofuran) to give Ar—C(=CH$_2$)—CH$_2$—OAc. In the third step, Ar—C(=CH$_2$)—CH$_2$—OAc is further reacted with KOH (potassium hydroxide) to finally obtain Ar—C(=CH$_2$)—CH$_2$—OH. Apart from the fact that this procedure makes use of 3 consecutive steps, each of which has to be carried out in a separate reaction vessel, it is noted that in particular as far as the second step is concerned, the reaction product is not easy to be separated from the by-product triphenylphosphine oxide.

Another procedure described in P. Blundell et al., Synlett 1994, pp. 263-265, starts from Ar—Br which, in a first step, is converted into a Grignard reagent which in turn is reacted with (Cl—CH$_2$)$_2$C=O (1,2-dichloro acetone) wherefrom Ar—C(OH)(CH$_2$Cl)$_2$ is obtained which, in a second step, is treated with potassium carbonate to obtain an epoxide. This epoxide, in turn, is then converted, in a third step, to Ar—C(=CH$_2$)—CH$_2$—OH. Apart from the fact that this procedure for manufacturing the allylic alcohol involves 3 steps, each of which has to be carried out in a separate reaction vessel, it is known that the Grignard reagent derived from Ar—Br, i.e. 2,4-difluoro bromobenzene, is a potentially hazardous compound.

WO 95/16658 A1 suggests another procedure for the preparation of Ar—C(=CH$_2$)—CH$_2$-L which starts from Ar—C(=O)—CH$_3$. In a Grignard reaction with consecutive elimination, the olefin compound Ar—C(=CH$_2$)—CH$_3$ is obtained which is then subjected to radical halogenation to obtain Ar—C(=CH$_2$)—CH$_2$-L (with L=Cl, Br). Compared to the two procedures discussed above, this procedure provides a process which, although involving 3 steps, can be carried out in only 2 reaction vessels, due to the fact that the Grignard reaction and the subsequent elimination are carried out in a single vessel. A major drawback of this procedure, however, has to be seen in the fact that the radical halogenation gives an undesired mixture of allyl halides and vinyl halides.

Therefore, it was an object of the present invention to provide an improved process for the preparation of a chiral compound of formula (IX) wherein the starting material, the compound of formula (II), is prepared by a novel process which is advantageous over said known prior art processes.

It was found that said starting material can be prepared by a process which can be carried out in only one single reaction vessel with good yields, wherein the process consists of only 2 reaction steps. Surprisingly, an olefination concept known as Peterson olefination could be applied for the preparation of above-mentioned allylic chloride. According to this olefination which is first described in "D. J. Peterson, Carbonyl olefination reaction using silyl-substituted organometallic compounds; J. Org. Chem. (1968) 33 (2) pp. 780-784", an alpha-silyl carbanion is reacted with ketones or aldehydes to form beta-hydroxysilanes which may eliminate to form alkenes. The vast majority of known examples using Peterson olefination are carried in diethyl ether which cannot be used in industrial scale processes due to safety aspects. In rare cases, tetrahydrofuran is described as an alternative solvent.

As discussed above, the compounds of formula (IX) and salts thereof are important intermediates for the preparation of antifungal agents. Due to several reasons, the presence of such intermediates as crystalline compounds is advantageous. However, from the known processes of the literature, compounds of formula (IX) and salts thereof, in particular compounds of formula (IX) with both $Y_1$ and $Y_2$ being F, are not obtained as at least partially crystalline compounds.

Therefore, it was another object of the present invention to provide a process from which the compound according to formula (IX) and salts thereof, in particular compounds of formula (IX) with both $Y_1$ and $Y_2$ being F, are obtained as at least partially crystalline compound.

It was yet another object of the present invention to provide the compound according to to formula (IX) and salts thereof, in particular compounds of formula (IX) with both $Y_1$ and $Y_2$ being F, as at least partially crystalline compound.

SUMMARY OF THE INVENTION

Therefore, the present invention relates to a process for the preparation of a chiral compound of formula (IX)

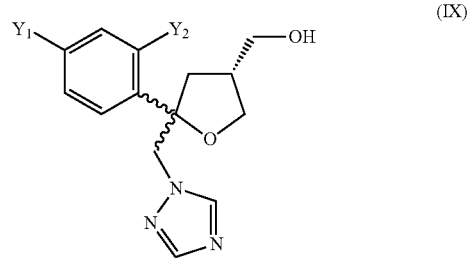

(IX)

or a salt thereof, wherein $Y_1$ and $Y_2$ are independently F or Cl, preferably F, the process comprising
(1.1) reacting a compound of formula (I)

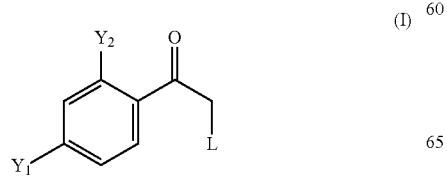

(I)

wherein L is a leaving group, preferably a halogen, more preferably Cl, in a solvent with a nucleophilic compound comprising a nucleophilic residue $R_aR_bR_cSi-CH_2$ wherein $R_a$, $R_b$ and $R_c$ are the same or different and selected from the group consisting of optionally suitably substituted alkyl and aryl residues, to obtain a reaction mixture containing as intermediate a beta-hydroxy silane of formula

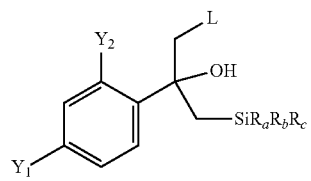

(1.2) treating the resulting reaction mixture, preferably without change of solvent, with a reagent promoting elimination reaction to obtain a reaction mixture containing a compound of formula (II)

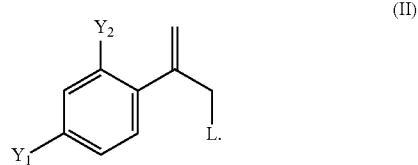

(II)

According to a particularly preferred embodiment, the present invention relates to a process as defined above wherein the compound of formula (IX) or a salt thereof

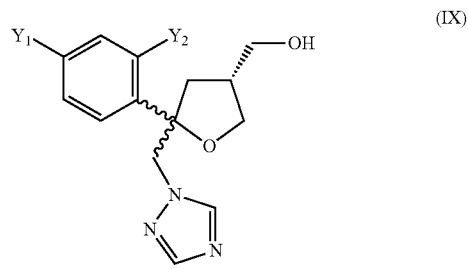

(IX)

is obtained which contains the cis-isomer of formula (VII) or the salt thereof

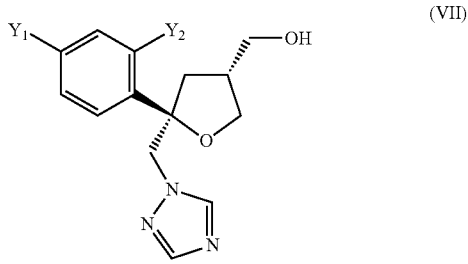

(VII)

as mixture with its trans-isomer of formula (VIII) or the salt thereof

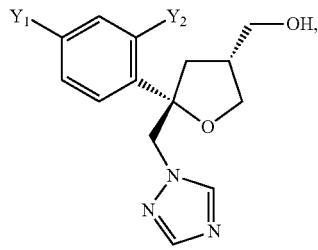

(VIII)

wherein preferably from 80 to 95%, more preferably from 85 to 95% of the molecules of the compound of formula (IX) or the salt thereof are present as cis-isomer of formula (VII) or the salt thereof and preferably from 20 to 5%, more preferably from 15 to 5% of the molecules of the compound of formula (IX) or the salt thereof are present as trans-isomer of formula (VIII) or the salt thereof.

Further, the present invention relates to a process wherein compound (IX), and thus also compound (VII), is crystallized from a solvent optionally by addition of a suitable antisolvent, wherein the solvent is preferably a polar water-immiscible solvent, preferably an ester such as ethyl acetate or isopropyl acetate, an ether such as tetrahydrofuran or methyl tetrahydrofuran, a ketone such as methyl isobutyl ketone, a halogenated solvent such as dichloromethane, toluene or a mixture of two or more of these solvents, more preferably an ester or an ether, more preferably an ether, and even more preferably methyl tetrahydrofuran, and wherein the antisolvent is preferably a saturated or unsaturated hydrocarbon such as cyclohexane, hexane, or heptane, or a mixture of two or more thereof.

Yet further, the present invention relates to a crystalline chiral compound of formula (IX) or a salt thereof

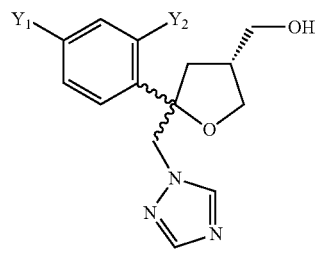

(IX)

wherein $Y_1$ and $Y_2$ are independently F or Cl, preferably F, and wherein from 80 to 95%, preferably from 85 to 95% of the molecules of said crystalline compound or the salt thereof are present as cis-isomer of formula (VII) or the salt thereof

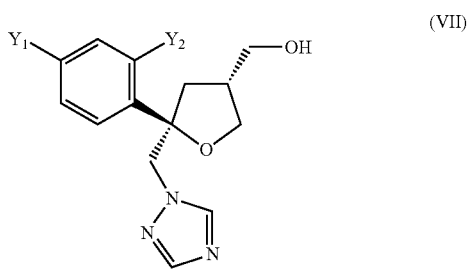

(VII)

and from 20 to 5%, preferably from 15 to 5% of the molecules of said crystalline compound or the salt thereof are present as trans-isomer of formula (VIII) or the salt thereof

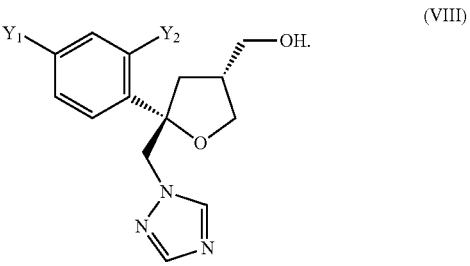

(VIII)

Still further, the present invention relates to the use of a compound of formula (IX) or a salt thereof, in particular of a preferably at least partially crystalline, preferably a crystalline compound of formula (IX) or a salt thereof, for the preparation of an antifungal agent, preferably posaconazole:

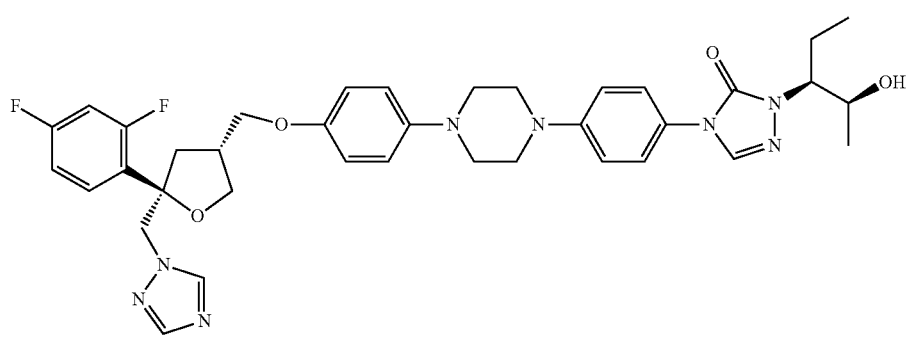 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

LIST OF FIGURES

Figure 1:
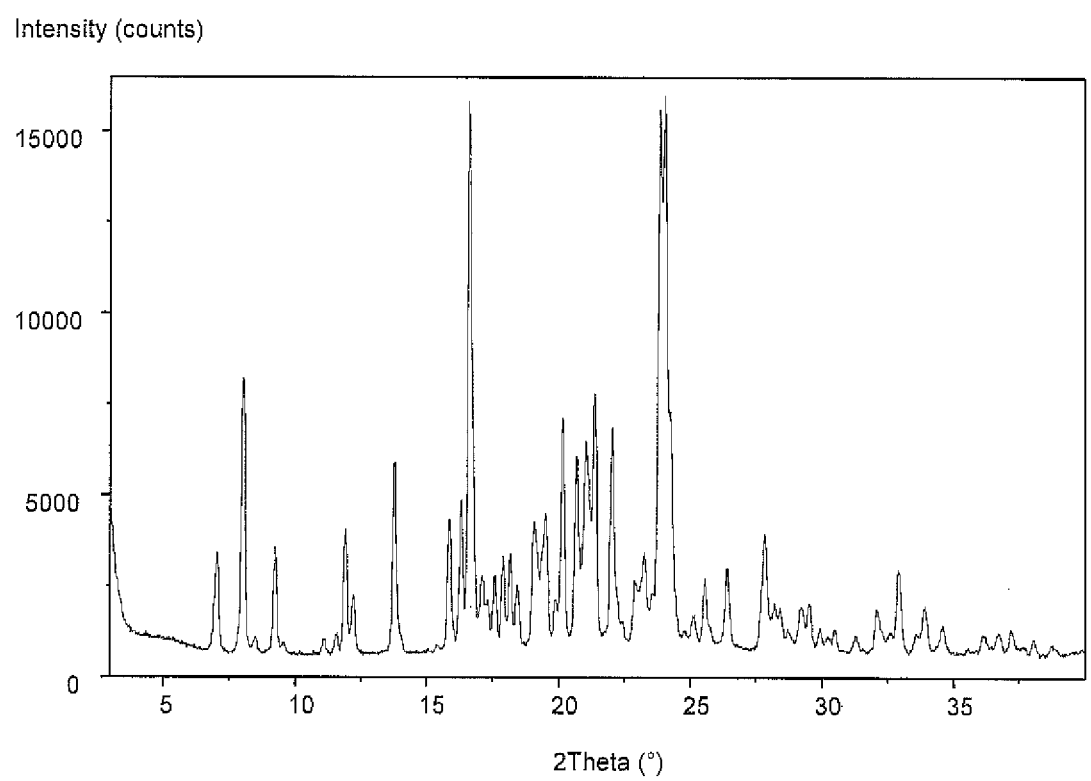
FIG. 1 shows the X-ray powder diffraction pattern (XRD) of the compound of formula (IXa) as obtained according to Example 1. The cis:trans ratio, i.e. the ratio compound of formula (VIIa): compound of formula (VIIIa) is 9:1.
Figure 2:
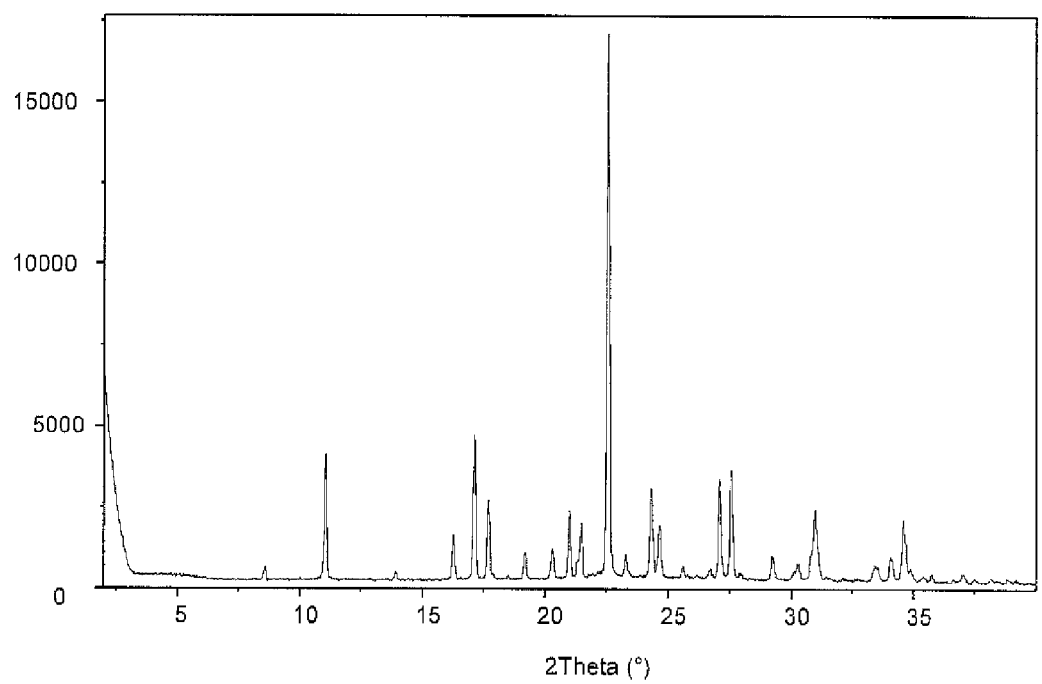
FIG. 2 shows the XRD of the HCl salt of compound of formula (IXa) as obtained according to Example 2(a). The cis:trans ratio, i.e. the ratio of the HCl salt of compound of formula (VIIa): the HCl salt of compound of formula (VIIIa) is 9:1.
Figure 3:
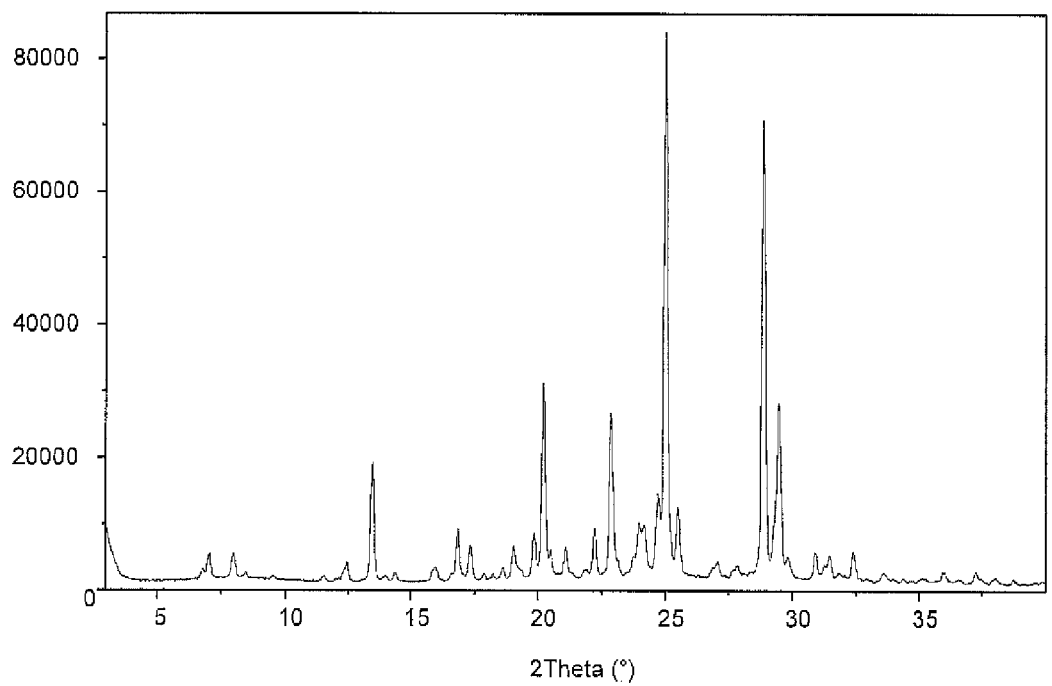
FIG. 3 shows the XRD of the fumaric acid salt of compound of formula (IXa) as obtained according to Example 2(b). The cis:trans ratio is indicated in the table shown in Example 2(b).
Figure 4:
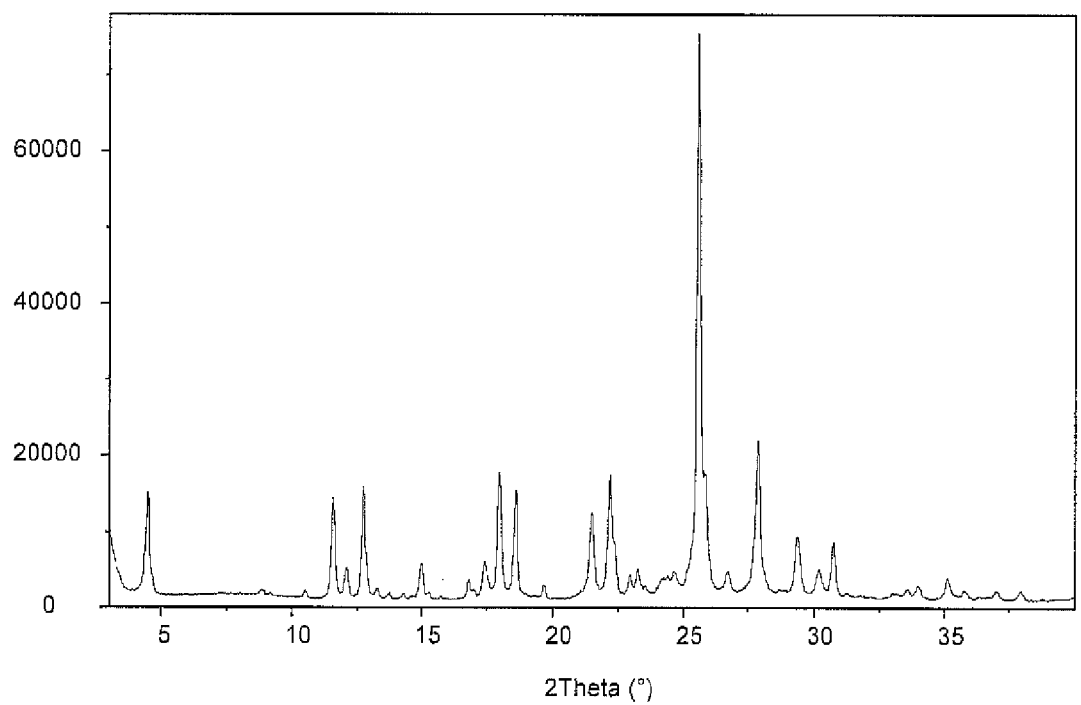
FIG. 4 shows the XRD of the oxalic acid salt of compound of formula (IXa) as obtained according to Example 2(b). The cis:trans ratio is indicated in the table shown in Example 2(b).
Figure 5:
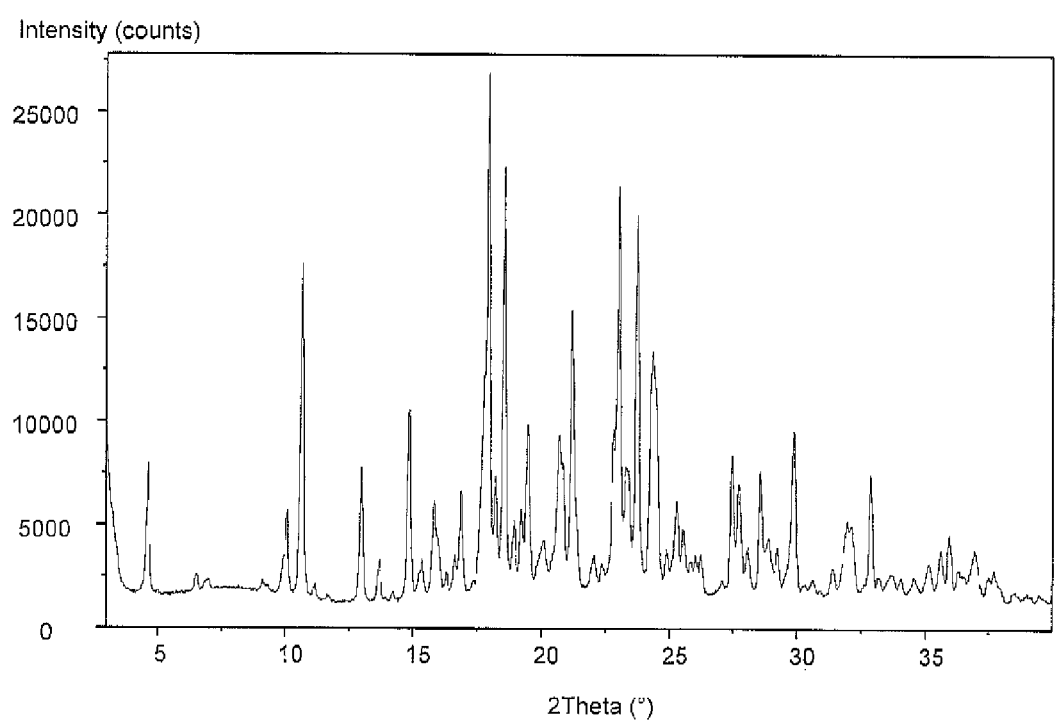
FIG. 5 shows the XRD of tartaric acid salt of compound of formula (IXa) as obtained according to Example 2(b). The cis:trans ratio is indicated in the table shown in Example 2(b).

In FIGS. 1 to 5, the intensity—measured as counts per second (linear scale)—is presented on the y-axis, while the position—expressed as 2 theta values in degrees—is presented on the x-axis.

DETAILED DESCRIPTION

According to the present invention, a compound of formula (II), in particular a reaction mixture containing a compound of formula (II), is obtained by a process which comprises (1.1) reacting a compound of formula (I)

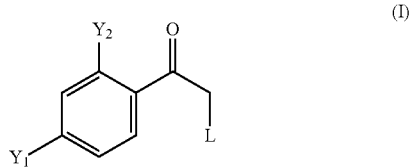

(I)

wherein L is a leaving group, preferably a halogen, more preferably Cl, in a solvent with a nucleophilic compound comprising a nucleophilic residue $R_aR_bR_cSi$—$CH_2$ wherein $R_a$, $R_b$ and $R_c$ are the same or different and selected from the group consisting of optionally suitably substituted alkyl and aryl residues, to obtain a reaction mixture containing as intermediate a beta-hydroxy silane of formula

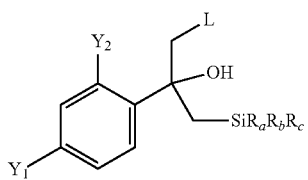

(1.2) treating the resulting reaction mixture, preferably without change of solvent, with a reagent promoting elimination reaction to obtain a reaction mixture containing a compound of formula (II)

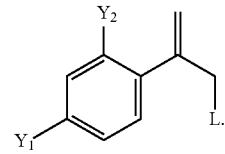

(II)

Steps (1.1) and (1.2)

In step (1.1) of the inventive process, the compound of formula (I) comprises residues $Y_1$ and $Y_2$. According to the present invention, $Y_1$ and $Y_2$ are independently F or Cl. Thus, $Y_1$ may be F or Cl, and independently from the chemical nature of $Y_1$, $Y_2$ may be F or Cl. Preferably, both $Y_1$ and $Y_2$ are either F or Cl. More preferably, both $Y_1$ and $Y_2$ are F.

The term "leaving group L" as used in the context of step (1.1) of the present invention refers to any chemical moieties L which, under suitable reaction conditions, departs from compound (I) with a pair of electrons in a heterolytic bond cleavage. For this purpose, compound (I) as used in the present invention may comprise any suitably leaving group L. Preferably, the leaving group L, after departing, is a neutral or an anionic moiety, more preferably an anionic moiety. Even more preferably, L is an halogen such as, for example, Cl, Br, I. According to an even more preferred embodiment of the present invention, L is Cl.

The nucleophilic compound with which compound (I) is reacted in step (1.1) comprises a nucleophilic residue $R_aR_b R_cSi$—$CH_2$. As to the chemical nature of this residue, there are no particular restrictions provided that the beta-hydroxy silane intermediate of formula

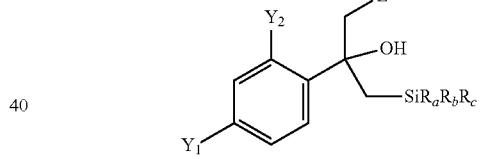

is obtained. The term "intermediate" as used in this context of the present invention generally refers to a beta-hydroxy silane which is comprised in the reaction mixture obtained in step (1.1) and which is formed from the reactants of step (1.1) and reacts further in (1.2). The term "intermediate" as used in this context does not exclude such beta-hydroxy silanes which can be isolated from the reaction mixture obtained in (1.1)

The nucleophilic compound employed in (1.1) can be any suitable compound comprising a nucleophilic residue $R_aR_b R_cSi$—$CH_2$ which, when reacted with compound (I), either directly or indirectly leads to the formation of the beta-hydroxy silane intermediate discussed above. $R_a$, $R_b$ and $R_c$ comprised in the nucleophilic compound are the same or different and selected from the group consisting of optionally suitably substituted alkyl and aryl residues. The term "optionally suitably substituted aryl residue" as used in the context of the present invention refers to aryl residues which have, for example, up to 6 or up to 12 carbon atoms. If such aryl residue is a substituted aryl residue, the number of carbon atoms refers to the number of carbon atoms of the corresponding unsubstituted aryl residue. The term "optionally suitably substituted alkyl residue" as used in the context of the present invention refers to alkyl residues which have, for example, 1 to 20, preferably 1 to 10 carbon atoms. If such alkyl residue is a substituted alkyl residue, the number of carbon atoms refers to the number of carbon atoms of the corresponding unsubstituted alkyl residue.

According to preferred embodiments of the present invention, $R_a$, $R_b$ and $R_c$ comprised in the nucleophilic compound are the same or different and selected from the group consisting of alkyl residues, more preferably non-substitued alkyl residues having from 1 to 6 carbon atoms, preferably from 1 to 4 carbon atoms such as methyl, ethyl, n-propyl, iso-propyl, n-butyl, iso-butyl, and tert-butyl, more preferably 1 or 2 carbon atoms, methyl or ethyl, with $R_a$, $R_b$ and $R_c$ in particular being methyl.

Preferably, the nucleophilic compound employed in (1.1) is a Grignard reagent. The term "Grignard reagent" as used in this context refers to any suitable nucleophilic organometallic reagent comprising the nucleophilic residue $R_aR_bR_cSi$—$CH_2$. Preferably the nucleophilic compound is a Grignard compound $R_aR_bR_cSi$—$CH_2MgX$ wherein X is a suitable anionic species which is preferably selected from the group consisting of Cl, Br, and I. More preferably, the Grignard compound is the compound $R_aR_bR_cSi$—$CH_2MgCl$.

As solvent which is employed in (1.1), any solvent or solvent mixture is conceivable, preferably a solvent or solvent mixture in which a Grignard reaction can be carried out. Conceivable solvents are, for example, ether compounds such as the commonly known diethyl ether and/or tetrahydrofuran (THF). Surprisingly, however, it was found in the context of the present invention that the solvents discussed in the background prior art in the context of the Peterson olefination, namely diethyl ether and THF, can be replaced by methyl-tert-butyl ether (MTBE). This solvent provides the major advantage that compared to compounds such as diethyl ether and THF, no peroxides are formed. Thus, the use of MTBE is especially suitable for industrial scale processes for which safety aspects are of utmost importance. Therefore, according to a particularly preferred embodiment, the solvent used in step (1.1) is MTBE.

Therefore, according to a preferred embodiment, the present invention relates to a process as defined above, wherein in (1.1), the compound of formula (I) is the compound (Ia)

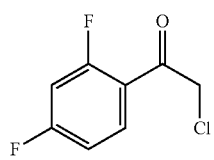
(Ia)

which is reacted in MTBE as solvent with the nucleophilic compound $(H_3C)_3Si$—$CH_2MgCl$ to obtain a reaction mixture containing as intermediate a beta-hydroxy silane of the formula:

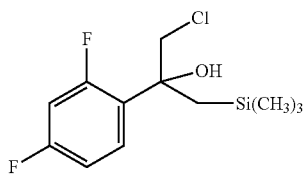

As to the temperatures at which the reaction in (1.1) is carried out, no particular restrictions exist provided a reaction mixture is obtained which allows for the reaction in (1.2). Preferably, reacting in (1.1) is performed at a temperature in the range of from −50 to +20° C., more preferably from −40 to +15° C., more preferably from −30 to +10° C., more preferably from −20 to +10° C., more preferably from −15 to +5° C. such as at a temperature in the range of from −15 to −10° C. or from −10 to −5° C. or from −5 to 0° C. or from 0 to +5° C.

As far as the general concept of the Peterson olefination is concerned, the literature teaches a two-step process wherein, after having carried out the Grignard reaction, a solvent exchange is performed. Reference is made to Tetrahedron Letters 32 (1991), pp. 7545-7548. Surprisingly, it was found that after step (1.1) of the present invention, no solvent exchange is necessary, and that the intermediate obtained from (1.1) can be treated with a suitable reagent which promotes elimination reaction in a considerably simplified process.

Therefore, according to the present invention, the reaction mixture resulting from (1.1) is treated in (1.2), preferably without change of solvent, with a reagent promoting elimination reaction to obtain a reaction mixture containing a compound of formula (II)

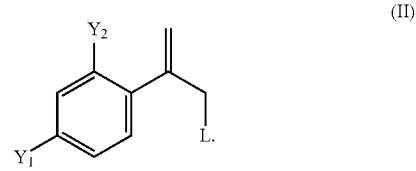
(II)

Since according to the literature, the second step of the Peterson olefination includes the use of $BF_3*Et_2O$ (boron trifluoride etherate), a further major advantage of the present invention is the fact that the use of potentially hazardous chemicals such as $BF_3$ etherate is completely avoided in this reaction stage. As discussed above, carrying out the inventive process without solvent exchange after (1.1) is particularly preferred if MTBE is used as solvent in (1.1).

As to the temperatures at which the reaction in (1.2) is carried out, no particular restrictions exist provided a reaction mixture is obtained containing the compound of formula (II). Preferably, treating in (1.2) is performed at a temperature in the range of from −20 to +70° C. Preferred temperature ranges are, for example, −20 to −10° C. or −10 to 0° C. or 0 to +10° C. or +10 to +20° C. or +20 to +30° C. or +30 to +40° C. or +40 to +50° C. or +50 to +60° C. or +60 to +70° C.

As to the reagent promoting elimination reaction employed in (1.2), no particular restrictions exist provided that the compound of formula (II) is obtained, preferably without solvent exchange after (1.1). Preferably, the reagent is an acid or a mixture of two or more acids. More preferably, the reagent is an inorganic acid or a mixture of two or more inorganic acids. Especially preferred is the use of sulfuric acid. Preferably, if sulfuric acid is used as reagent, the temperature at which (1.2) is performed is in the range of from +40 to +50° C.

Therefore, according to a preferred embodiment, the present invention relates to a process as defined above, wherein in (1.2), the reaction mixture resulting from (1.1) is treated without change of solvent with sulfuric acid promoting elimination reaction to obtain a reaction mixture containing, as compound of formula (II), the compound (IIa):

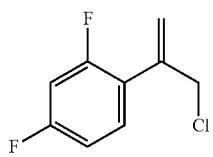
(IIa)

Thus, according to a still more preferred embodiment, the present invention relates to a process as defined above which comprises
(1.1) reacting a compound of formula (Ia)

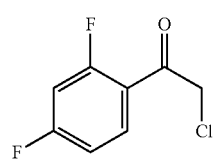
(Ia)

with (H$_3$C)$_3$Si—CH$_2$MgCl in MTBE as solvent to obtain a reaction mixture containing as intermediate a beta-hydroxy silane of formula

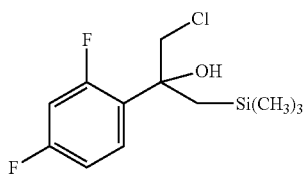

(1.2) treating the resulting reaction mixture without change of the solvent MTBE with sulfuric acid promoting elimination reaction to obtain a reaction mixture containing a compound of formula (IIa)

(IIa)

According to a still more preferred embodiment, the present invention relates to a process as defined above which comprises
(1.1) reacting a compound of formula (Ia)

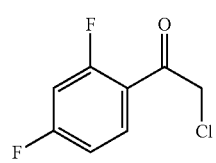
(Ia)

with (H$_3$C)$_3$Si—CH$_2$MgCl in MTBE as solvent at a temperature in the range of from −15 to +5° C. to obtain a reaction mixture containing as intermediate a beta-hydroxy silane of formula

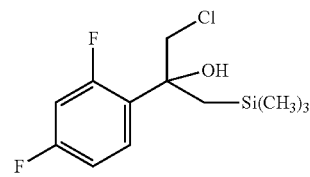

(1.2) treating the resulting reaction mixture without change of the solvent MTBE at a temperature in the range of from +40 to +50° C. with sulfuric acid promoting elimination reaction to obtain a reaction mixture containing a compound of formula (IIa)

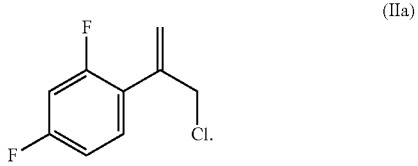
(IIa)

From the compound contained in the reaction mixture obtained in (1.2) as discussed above, the compound of formula (IX) is prepared. As far as specific sequences of individual reaction steps leading from the compound of formula (II) to the compound of formula (IX) are concerned, no particular restrictions exist. According to a preferred sequence of reaction steps, the process of the present invention as defined above further comprises (2) reacting the compound of formula (II) with a malonic ester R$_1$OOC—CH$_2$—COOR$_2$ to obtain a compound of formula (III)

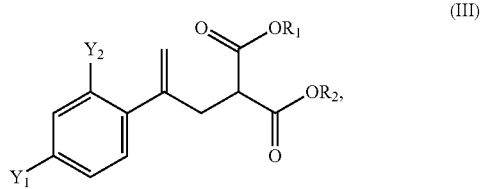
(III)

wherein R$_1$ and R$_2$ are independently an optionally suitably substituted alkyl group having from 1 to 5 carbon atoms;

(3) reducing the compound of formula (III) to obtain a compound of formula (IV)

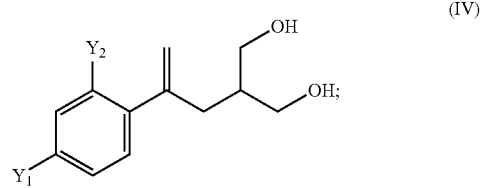
(IV)

(4) acylating the compound of formula (IV) with isobutyric anhydride to obtain a compound of formula (V)

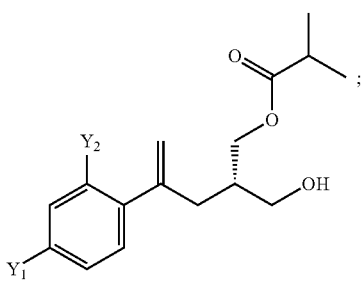

(5) reacting the compound of formula (V) with a halogen $Hal_2$ selected from the group consisting of $Cl_2$, $Br_2$ and $I_2$, preferably $I_2$, in the presence of a base in a solvent to obtain a compound of formula (X)

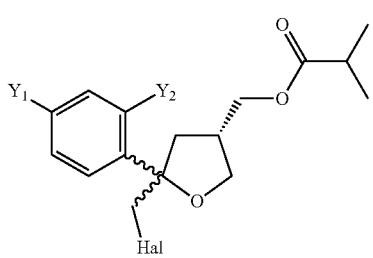

(6.1) heating the compound of formula (X), preferably in the absence of DMPU (1,3-dimethyl-3,4,5,6-tetrahydro-2 (1H)-pyrimidinone), in a solvent, preferably DMSO (dimethyl sulfoxide), with a 1,2,4-triazole alkali metal salt, preferably the sodium salt, and treating the resulting reaction mixture with a base, to obtain a compound of formula (IX)

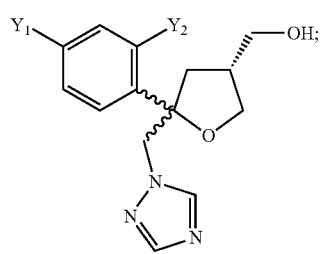

(6.2) separating the compound of formula (IX) from the reaction mixture obtained from (6.1) by extraction in a suitable solvent.

Step (2)

According to step (2) of the present invention, the compound of formula (II) is preferably reacted with a malonic ester $R_1OOC$—$CH_2$—$COOR_2$ wherein $R_1$ and $R_2$ are independently an optionally suitably substituted alkyl group having from 1 to 5 carbon atoms. The number of carbon atoms refers to the number of carbon atoms of the unsubstituted alkyl residue. Preferred alkyl groups $R_1$ and $R_2$ have 1 to 4 carbon atoms, such as methyl, ethyl, n-propyl, iso-propyl, n-butyl, iso-butyl, and tert-butyl. Even more preferably the alkyl groups $R_1$ and $R_2$ have 1 or 2 carbon atoms, such as methyl or ethyl, with ethyl being especially preferred. Even more preferably, the alkyl groups $R_1$ and $R_2$ are unsubstituted alkyl groups.

In step (2), it is further preferred to react the malonic ester $R_1OOC$—$CH_2$—$COOR_2$ with compound (II) in the presence of a suitable strong base, preferably a strong alkali metal base allowing for the reaction of the respective anion $^-CH$ $(COOR_1)(COOR_2)$ derived from the malonic ester $R_1OOC$—$CH_2$—$COOR_2$. As alkali metal, sodium is preferred. Suitable bases are, for example, NaH or NaOH, with NaOH being preferred. NaOH can be employed in every suitable form. According to a preferred embodiment, NaOH is employed as solid, such as, for examples, in the form of NaOH flakes. The solvent in which step (2) is carried out can be chosen according to, for example, the specific chemical nature of the strong base as discussed above. Conceivable solvents are, for example, THF, DMSO or the like. According to present invention, DMSO is preferred. The temperatures at which the reaction in step (2) is carried out can be chosen in accordance with the solvent and the base. Preferred temperatures are in the range of from 0 to 35° C., more preferably from 25 to 30° C.

The product of the reaction in (2), the compound of formula (III)

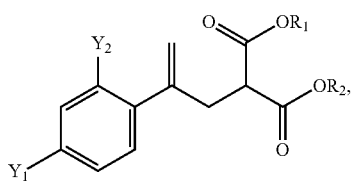

is preferably suitably separated from the reaction mixture obtained in (2). According to a preferred embodiment, this separation includes a step wherein the compound (III) is separated by extraction in a suitable solvent. Among the suitable solvents, cyclohexane is preferred according to present invention.

The organic layer obtained from extraction can be washed in one or more steps. As washing agents, water and aqueous basic solutions such as, for example, aqueous solutions of alkali metal bases such as alkali metal hydroxide, preferably sodium hydroxide, are to be mentioned.

Step (3)

According to a further preferred embodiment of the present invention, the compound of formula (III) obtained from step (2) is suitably reduced wherefrom a compound of formula (IV) is obtained:

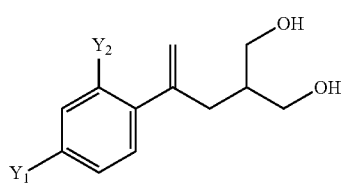

Reducing in step (3) can be carried out according to any suitable method involving any suitable reducing agent. According to the present invention, the use of a hydride reducing agent is preferred. Such hydride reducing agents are, for example, sodium borohydride ($NaBH_4$), lithium borohydride ($LiBH_4$), lithium aluminium hydride ($LiAlH_4$), diisobutylaluminium hydride (DIBAL) or lithium triethylborohydride (LiEt$_3$BH). According to a preferred embodiment of the present invention, LiBH$_4$ is employed as reducing agent in step (3).

According to the prior art, at least 3 molar equivalents of LiBH$_4$ have to be employed with regard to the compound of formula (III). Reference is made to WO 94/25452, page 31, section "Preparation 5". Surprisingly, however, contrary to the teaching of the prior art, the reducing agent LiBH$_4$ can be employed in a much lower excess with regard to the malonic ester compound (III). The improved process of the present invention uses at most 2 molar equivalents of LiBH$_4$ with regard to the compound of formula (III), which means that compared to the prior art, at least 33% of reducing agent can be saved. Thus, in particular for an industrial scale process, the present invention provides economical and ecological advantages. Thus, the present invention relates a process as defined above, wherein LiBH$_4$ is used as reducing agent which is preferably used in an amount of at most 2 molar equivalents with respect to compound (III).

As to the solvent in which the reaction of step (3) is carried out, no particular restrictions exist provided that the compound of formula (IV) is obtained. Preferred solvents are selected from the group consisting of water, alcohol, and a mixture of water and at least one alcohol. Preferred alcohols are methanol, ethanol, and isopropanol. Therefore, the solvent is preferably selected from the group consisting of water, methanol, ethanol, isopropanol, and a mixture of water and at least one of these alcohols, more preferably from the group consisting of water, ethanol, isopropanol, and a mixture of water and at least one of these alcohols, more preferably from the group consisting of water, isopropanol, and a mixture of water and isopropanol.

Surprisingly, it was found that in particular for the most preferred reducing agent used in step (3), LiBH$_4$, a mixture of water and isopropanol is the most advantageous solvent. Contrary to the fact that water is known as decomposing hydride reducing agent, the presence of water was found to be advantageous in step (3) of the inventive process. Without wanting to be bound to any theory, it is believed that this could be due to the fact that a certain amount of water improves the solubility of the reagent LiBH$_4$, and/or of its precursors NaBH$_4$ and LiCl, and thus enhances the reaction rate, and thus in turn overcompensates the decomposition of the reducing agent. Therefore, according to still further embodiments, the solvent used in step (3) comprises water, wherein the solvent preferably comprises from 1 to 20 vol.-%, more preferably from 5 to 15 vol.-% of water.

The temperatures at which the reaction in step (3) is carried out can be chosen in accordance with the solvent and the reducing agent. Preferred temperatures are in the range of from 0 to 40° C., more preferably from 20 to 35° C., more preferably from 25 to 30° C.

The product of the reduction in (3), the compound of formula (IV), is preferably suitably separated from the reaction mixture obtained in (3). According to a preferred embodiment, this separation includes a step wherein the compound (IV) is separated by extraction in a suitable solvent. Among the suitable solvents, toluene is preferred according to the present invention.

Step (4)

According to step (4) of the present invention, the compound of formula (IV) is preferably acylated with isobutyric anhydride to obtain a compound of formula (V)

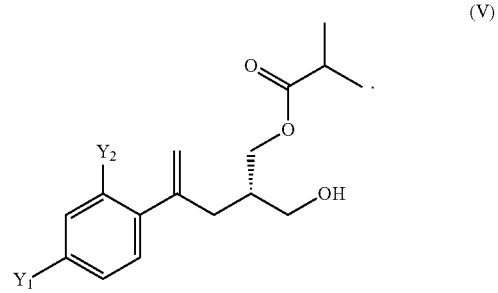

More preferably acylation in (4) is carried out in the presence of a suitable enzyme, preferably Novo SP 435 enzyme in a suitable solvent, preferably acetonitrile or toluene, more preferably toluene, e.g. analogously to the method described in WO 97/22710. The choice of toluene as solvent is also beneficial in extractive work up as no additional solvent is required. In case of acetonitrile as solvent it is required to use an additional immiscible solvent for extractive work up.

The temperatures at which the acylation in step (4) is carried out can be chosen in accordance with the solvent, the acylation agent and the enzyme. Preferred temperatures are in the range of from −20 to −5° C., more preferably from −15 to −10° C., more preferably from 25 to 30° C.

The obtained reaction mixture is preferably further treated with a suitable base such as, for example, sodium hydrogencarbonate.

According to an especially preferred embodiment of the present invention, the compound of formula (V) is suitably crystallized from the reaction mixture. Therefore, the present invention also relates to a process as defined above wherein after (4) and before (5), the compound of formula (V) is at least partially crystallized. Crystallization can be carried out according to any conceivable method. According to a preferred embodiment, the compound if formula (V) is crystallized from n-heptane.

Step (5)

According to step (5) of the present invention, the compound of formula (V) is preferably reacted with a halogen Hal$_2$ selected from the group consisting of Cl$_2$, Br$_2$ and I$_2$, to preferably I$_2$, in the presence of a base in a solvent to obtain a compound of formula (VI)

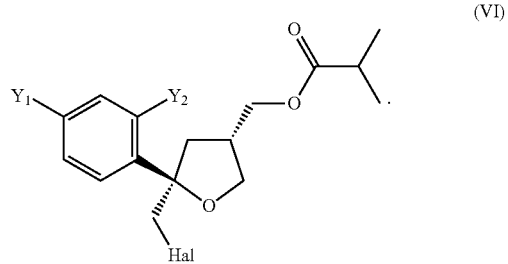

Generally, it is possible to carry out the reaction in step (5) in the presence of a base such as pyridine and in a suitable solvent such as acetonitrile, THF, EtOAc (ethyl acetate) or CH$_2$Cl$_2$ (dichloromethane, DCM) at a temperature in the range of from −20 to +30° C. Reference is made to WO 94/25452 A1, pages 16 and 35. However, in the context of the present invention, it was found that the reaction is suitably carried out in ethyl acetate as solvent wherein as base, sodium hydrogencarbonate is employed. Thus, the present invention provides a process which allows for replacing the non-harmless base pyridine. Further, it was found that the temperature for carrying out the reaction is preferably less than 0° C., more preferably not higher than −5° C. and even more preferably not higher than −10° C.

After the reaction, the organic layer, optionally after suitable quenching, may be optionally washed at least once. Quenching may be done e.g. using a 10% (w/v) aqueous solution of sodium sulphite.

According to a particularly preferred embodiment, the present invention relates to a process as defined above wherein the compound of formula (VI), the cis-isomer, is obtained in step (5) together with the compound of formula (XI), the respective trans-isomer

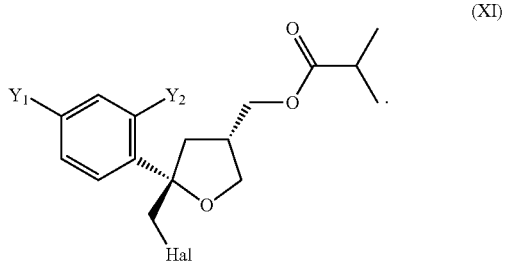

This mixture of the compounds of formula (VI) and (XI) is referred to in the following as compound of formula (X)

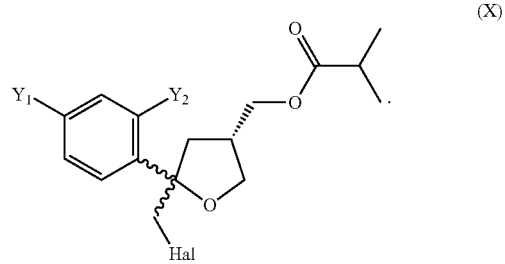

In said compound (X), according to the present invention, preferably from 80 to 95%, more preferably from 85 to 95% of the molecules are present as cis-isomer of formula (VI) and preferably from 20 to 5%, more preferably from 15 to 5% of the molecules of compound (X) are present as trans-isomer of formula (XI).

Therefore, the present invention also relates to the process as defined above, further comprising (5) reacting the compound of formula (V) with a halogen $Hal_2$ selected from the group consisting of $Cl_2$, $Br_2$ and $I_2$, preferably $I_2$, in the presence of a base in a solvent to obtain a compound of formula (X)

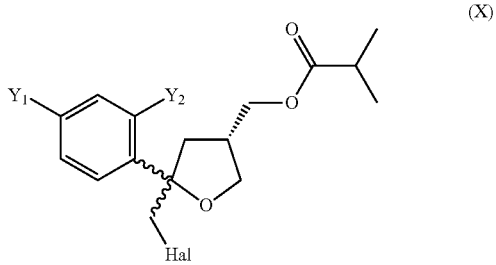

wherein preferably from 80 to 95%, more preferably from 85 to 95% of the molecules of compound (X) are present as cis-isomer of formula (VI) and preferably from 20 to 5%, more preferably from 15 to 5% of the molecules of compound (X) are present as trans-isomer of formula (XI).

The compound of formula (X) is suitable for the preparation of a compound of formula (IX) as herein described.

Step (6.1)

According to step (6.1) of the present invention, the compound of formula (X), i.e. in particular the compound of formula (VI) and the compound of formula (XI), is preferably suitably heated in a suitable solvent with a suitable 1,2,4-triazole salt. Preferred 1,2,4-triazole salts are alkali metal salts, with the sodium salt being especially preferred. Preferred solvents are polar aprotic solvents, for example, DMF (N,N-dimethylformamide) and DMSO, with DMSO being preferred.

The temperature to which the reaction mixture in step (6.1) is heated is preferably in the range of from +70 to +100° C., preferably from +80 to +95° C. and more preferably from +85 to +90° C.

As to such reactions with a triazole salt, WO 94/25452 teaches that such heating has to be carried out in the presence of 1,3-dimethyl-3,4,5,6-tetrahydro-2(1H)-pyrimidinone (DMPU). Reference is made to page 17, step (1), and page 39, step (b) of WO 94/25452. Surprisingly, contrary to the teaching in WO 94/25452, it was found that heating the compound of formula (X) in step (6.1) can be performed in the absence of DPMU. Thus, according to the considerably improved process of the present invention, a simplified solvent system is provided which, according to a preferred embodiment, consists of DMSO only, i.e. of only one solvent compound contrary to the mandatory 2 compound system as taught in WO 94/25452.

The mixture obtained from heating is then preferably treated with a suitable base to promote saponification of the ester moiety. Such bases are, for example, alkali metal hydroxides, alkali metal bicarbonates, alkali metal carbonates, alkaline earth metal hydroxides, alkaline earth metal bicarbonates, and alkaline earth metal carbonates. The alkali metal bases are preferred. Preferably, the base is added in aqueous and/or alcoholic media. Suitable alcohols are alcohols containing 1 to 6, preferably 1 to 4, more preferably 1 to 3, most preferably 1 to 2 carbon atoms. According to the present invention, it was found that a preferred base is sodium hydroxide, preferably employed as aqueous solution, in the presence of methanol.

According to the present invention, in step (6.1), a compound of formula (IX)

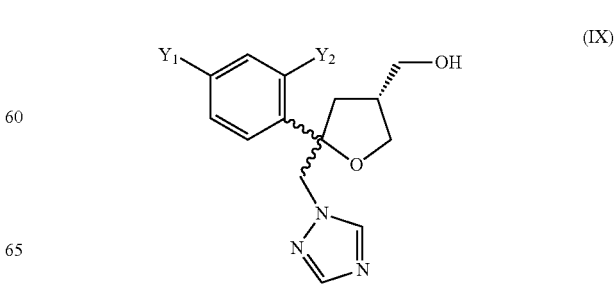

is obtained, wherein preferably from 80 to 95%, more preferably from 85 to 95% of the molecules are present as cis-isomer of formula (VII)

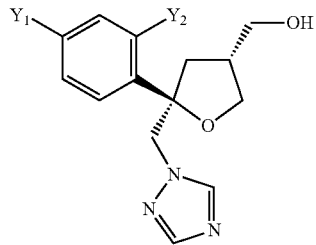

and preferably from 20 to 5%, more preferably from 15 to 5% of the molecules are present as trans-isomer of formula (VIII)

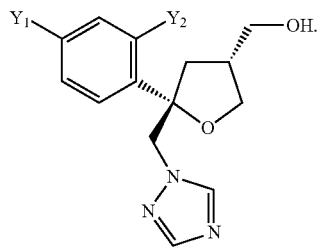

According to the prior art, it is necessary to separate the compound of formula (IX) and thus of formula (VII), after reaction steps corresponding to step (6.1) of the present invention by chromatography. Reference is made to WO 94/25452, page 39, step (b). Thus, the prior art explicitly teaches that a costly and time-consuming purification has to be performed which renders the known process considerably detrimental concerning its industrial-scale application.

Contrary to the teaching of the prior art, it was found in the context of the present invention that no such separation by chromatography has to be carried out if the specific sequence of steps (6.1) and extraction in (6.2), preferably followed by crystallization in a step (7) and/or salt formation in a step (8) as described below is carried out. Thus, this modification represents a considerable improvement over the prior art processes.

Step (6.2)

According to step (6.2) of the present invention, the compound of formula (IX)

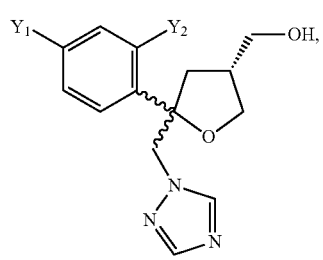

in particular the compound of formula (VII)

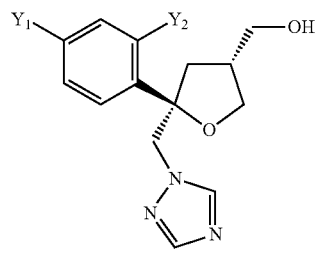

and the compound of formula (VIII),

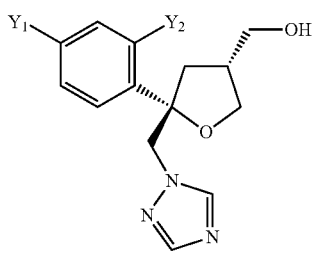

comprised in the mixture obtained from step (6.1) is suitably separated, preferably by extraction into a suitable solvent.

Preferred solvents according to the present invention are polar water-immiscible solvents. More preferably, the solvent is an ester such as ethyl acetate or isopropyl acetate, an ether such as tetrahydrofuran or methyl tetrahydrofuran, a ketone such as methyl isobutyl ketone, a halogenated solvent such as dichloromethane, toluene, or a mixture of two or more of these solvents, more preferably an ester or an ether, more preferably an ether, and even more preferably methyl tetrahydrofuran.

After separation by extraction, at least one washing stage may be carried out. Among others, washing with an aqueous sodium chloride solution may be mentioned.

Therefore, according to a preferred embodiment, the present invention relates to a process defined above, comprising (1.1) reacting a compound of formula (Ia)

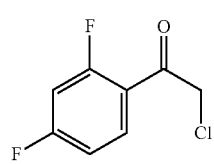

with $(H_3C)_3Si\text{—}CH_2MgCl$ in MTBE as solvent to obtain a reaction mixture containing as intermediate a beta-hydroxy silane of formula

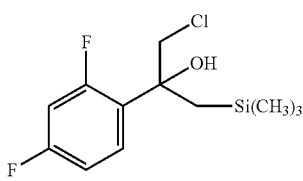

(1.2) treating the resulting reaction mixture without change of the solvent MTBE with sulfuric acid promoting elimination reaction to obtain a reaction mixture containing a compound of formula (IIa)

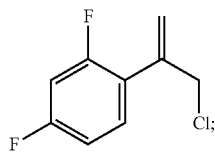
(IIa)

(2) reacting the compound of formula (IIa) with a malonic ester H₃CH₂COOC—CH₂—COOCH₂CH₃ to obtain a compound of formula (IIIa)

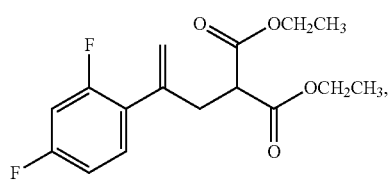
(IIIa)

(3) reducing the compound of formula (IIIc) using LiBH₄ as reducing agent which is used in an amount of at most 2 molar equivalents with respect to compound (IIIa) in a mixture of water and isopropanol as solvent to obtain a compound of formula (IVa)

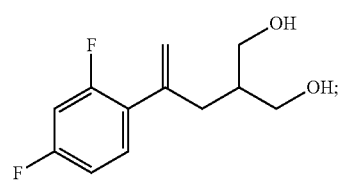
(IVa)

(4) acylating the compound of formula (IVa) with isobutyric anhydride in the presence to of Novo SP 435 enzyme in toluene as solvent to obtain a compound of formula (Va)

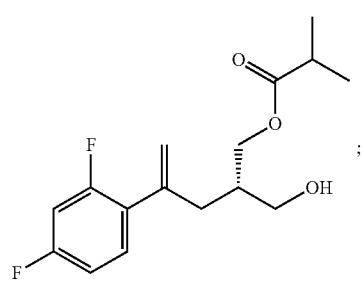
(Va)

(5) reacting the compound of formula (Va) with I₂ in the presence of sodium hydrogencarbonate as base in ethyl acetate as solvent to obtain a compound of formula (Xa)

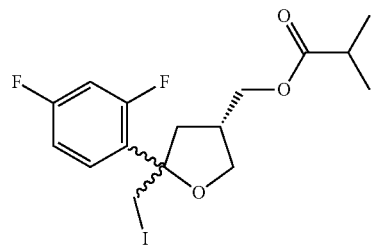
(Xa)

wherein preferably from 80 to 95%, more preferably from 85 to 95% of the molecules of compound (Xa) are present as cis-isomer of formula (VIa)

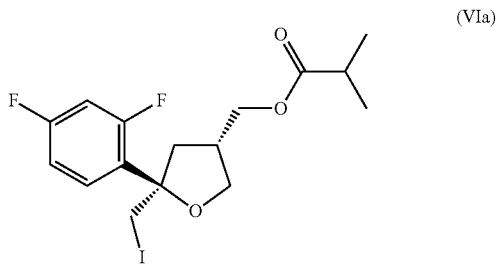 [SMILES: CC(C)C(=O)OC[C@@H]1CO[C@@](CI)(c2ccc(F)cc2F)C1]
(VIa)

and preferably from 20 to 5%, more preferably from 15 to 5% of the molecules of compound (Xa) are present as trans-isomer of formula (XIa)

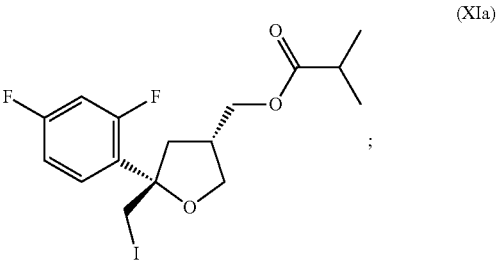 [SMILES: CC(C)C(=O)OC[C@@H]1CO[C@](CI)(c2ccc(F)cc2F)C1]
(XIa)

(6.1) heating the compound of formula (Xa), preferably in the absence of DMPU (1,3-dimethyl-3,4,5,6-tetrahydro-2 (1H)-pyrimidinone), in DMSO as solvent with 1,2,4-triazole sodium salt and treating the resulting reaction mixture with sodium hydroxide, to obtain a compound of formula (IXa)

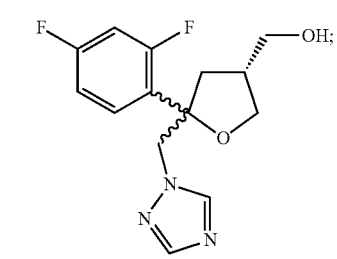
(IXa)

wherein in the compound of formula (IXa), from 80 to 95%, preferably from 85 to 95% of the molecules are present as cis-isomer of formula (VIIa)

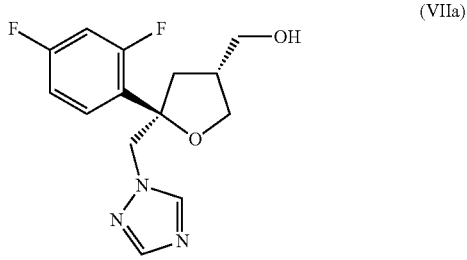 [SMILES: OC[C@@H]1CO[C@@](Cn2cncn2)(c2ccc(F)cc2F)C1]

(VIIa)

and from 20 to 5%, preferably from 15 to 5% of the molecules are present as trans-isomer of formula (VIIIa)

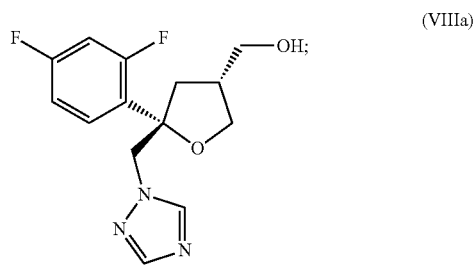 [SMILES: OC[C@@H]1CO[C@](Cn2cncn2)(c2ccc(F)cc2F)C1]

(VIIIa)

(6.2) separating the compound of formula (IXa)

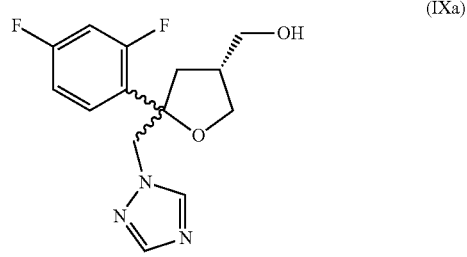

(IXa)

from the reaction mixture obtained from (6.1) by extraction with methyl tetrahydrofuran.

According to one preferred embodiment of the present invention, the compound of formula (IX) and thus also of formula (VII) as obtained from step (6.2) is suitably and at least partially crystallized in a step (7). Therefore, the present invention also relates to a process as defined above, which further comprises (7) at least partially crystallizing the compound of formula (IX), in particular the compound of formula (VII) and the compound of formula (VIII), after (6.2), Step (7)

As far as this crystallization is concerned, no particular restrictions exist. According to a preferred embodiment of the present invention, the solvent from which the compound of formula (IX), in particular the compound of formula (VII) and the compound of formula (VIII), is crystallized is the solvent which has been employed in step (6.2) discussed above for the extraction purposes. Therefore, preferred solvents of step (7) are polar water-immiscible solvents. More preferably, the solvent is an ester such as ethyl acetate or isopropyl acetate, an ether such as tetrahydrofuran or methyl tetrahydrofuran, a ketone such as methyl isobutyl ketone, a halogenated solvent such as dichloromethane, toluene, or a mixture of two or more of these solvents, more preferably an ester or an ether, more preferably an ether, and even more preferably methyl tetrahydrofuran.

Even more preferably, after step (6.2), no solvent exchange is performed. Thus, according to this preferred embodiment, the compound of formula (IX), in particular the compound of formula (VII) and the compound of formula (VIII), is crystallized from the mixture obtained in step (6.2) without addition of a further suitable solvent different from the solvent employed in step (6.2).

Generally, such crystallization can be carried out according to any suitable method. Among others, cooling the mixture obtained from (6.2), addition of an antisolvent to the mixture obtained from (6.2), suitable chemical reaction, change of the pH in the mixture obtained from (6.2), solvent distillation, or a combination of two or more of these methods may be mentioned.

According to a still further preferred embodiment, this crystallization in step (7) is carried out by adding a suitable antisolvent. Generally, depending on the solvent employed in (6.2), every conceivable antisolvent can be employed provided that this antisolvent allows for reducing the solubility of the dissolved compound of formula (IX), in particular the compound of formula (VII) and the compound of formula (VIII), to such an extent that the compound of formula (IX) is at least partially crystallized. Preferably, the antisolvent is a saturated or unsaturated hydrocarbon such as cyclohexane, hexane, or heptane, or a mixture of two or more thereof. Even more preferably, the antisolvent used in step (7) is selected from the group consisting of cyclohexane, hexane, heptane, and a mixture of two or more thereof, in particular heptane.

Generally, the temperatures at which crystallization in step (7) is performed are adjusted to the solvent and preferably the antisolvent used. According to a preferred embodiment of the present invention, addition of the antisolvent is performed at a temperature in the range of from 40 to 70° C., preferably from 45 to 65° C., and more preferably from 50 to 60° C. Thereafter, it is preferred to cool the resulting mixture continuously to a preset temperature wherein cooling can be carried out continuously, or step-wise in two or more steps. According to an embodiment of the present invention, the preset temperature to which the mixture is ultimately cooled is in the range of from −15 to 0° C., preferably from −10 to 0° C., more preferably from −5 to 0° C. Cooling the mixture to this temperature can, as mentioned above, involve at least one temperature range to which the mixture is cooled in a first step, held at this temperature, and then further cooled to the final temperature discussed above. For example, such temperature range to which the mixture can be cooled in a first step is from 20 to 35° C., preferably from 25 to 30° C.

After crystallization, the crystallized compound of (IX), in particular the crystallized compound of formula (VII) and the crystallized compound of formula (VIII), is preferably separated from the mother liquor, for example by suitable filtration, and preferably washed at least once with a suitable washing agent. Preferred washing agents are the solvent mixture used for the crystallization and the antisolvent discussed above. After such preferred separation, the crystallized compound of formula (IX), in particular the crystallized compound of formula (VII) and the crystallized compound of formula (VIII), is preferably dried under suitable drying conditions. Drying in vacuo is preferred wherein the temperatures are preferably in the range of from 20 to 50° C., more preferably from 30 to 45° C.

According to the process of the present invention, and as described above, the crystalline chiral compound of formula (VII), the cis-isomer

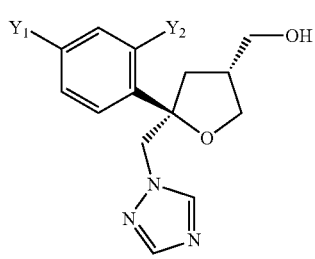

(VII)

is obtained as mixture with its diasteromeric form, the crystalline compound of formula (VIII), namely the trans-isomer

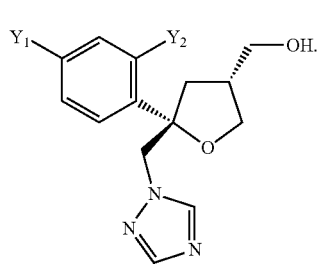

(VIII)

The molar ratio of the cis-isomer to the trans-isomer generally depends on the overall process conditions. According to preferred process conditions of the process of the present invention, the crystallized compound of formula (IX) obtained after step (7),

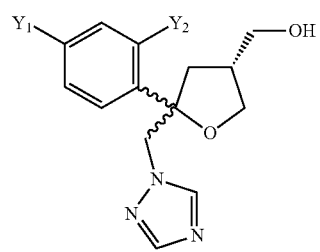

(IX)

contains from 80 to 95%, preferably from 85 to 95% of the cis-isomer (VII) and from 20 to 5%, preferably from 15 to 5% of the trans-isomer (VIII). Therefore, the present invention also relates to the process as defined above, wherein an at least partially crystalline chiral compound of formula (IX)

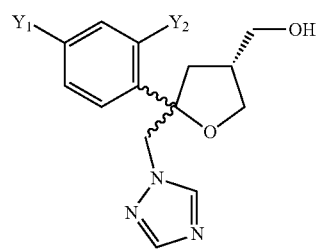

(IX)

is obtained, wherein from 80 to 95%, preferably from 85 to 95% of the molecules of said crystalline compound are present as the cis-isomer of formula (VII)

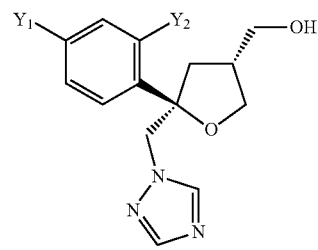

(VII)

and from 20 to 5%, preferably from 15 to 5% of the molecules of said crystalline compound are present as the trans-isomer of formula (VIII)

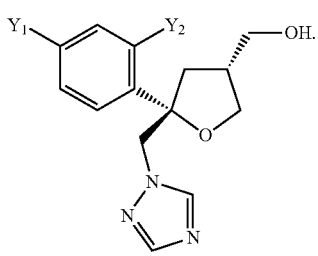

(VIII)

According to the prior art, the preparation of the crystalline compound of formula (IX), i.e. a crystalline mixture preferably containing 80 to 95%, more preferably from 85 to 95% of the cis-isomer (VII), and preferably from 20 to 5%, more preferably from 15 to 5% of the trans-isomer of (VIII), are not taught. Reference is made to WO 94/25452, page 39, step (b) where it is disclosed that costly and time-consuming purification by column chromatography has to be performed which leads to non at least partly crystalline compound (IX). However, it is believed that the mixture of compounds (VII) and (VIII) as obtained according to the present invention can be similarly used as key compound for further reactions, in particular as key compound for the preparation of an antifungal agent such as, in particular, posaconazole.

Thus, the present invention also relates to a crystalline chiral compound of formula (IX) or a salt thereof

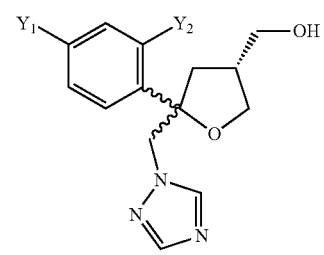

(IX)

wherein $Y_1$ and $Y_2$ are independently F or Cl, preferably F, and wherein from 80 to 95%, preferably from 85 to 95% of the molecules of said crystalline compound or the salt thereof are present as cis-isomer of formula (VII) or the salt thereof

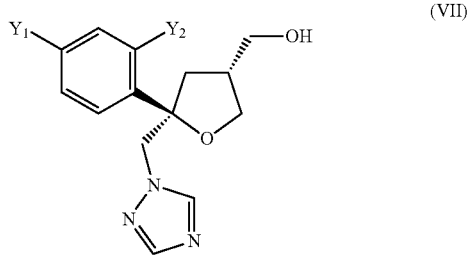

(VII)

and from 20 to 5%, preferably from 15 to 5% of the molecules of said crystalline compound or the salt thereof are present as trans-isomer of formula (VIII) or the salt thereof

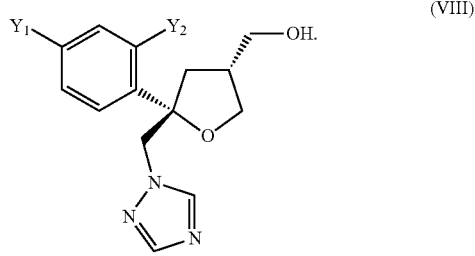

(VIII)

The crystalline chiral compound of formula (IX) as herein described, wherein $Y_1$ and $Y_2$ are F, preferably exhibits the following X-ray diffraction pattern comprising at least the following reflections:

| Diffraction angle °2 Theta [Cu K(alpha 1)] | Relative Intensity (%) |
|---|---|
| 7.05 | 19 |
| 8.03 | 51 |
| 9.25 | 20 |
| 11.92 | 24 |
| 13.79 | 36 |
| 15.88 | 25 |
| 16.65 | 100 |
| 20.15 | 42 |
| 21.37 | 45 |
| 22.04 | 37 |
| 24.04 | 96 |
| 27.80 | 20 | wherein 100% relates to the intensity of the maximum peak in the X-ray diffraction pattern.

Based on the crystalline compound of formula (IX) preferably containing from 80 to 95%, preferably from 85 to 95% of the cis-isomer (VII) and from 20 to 5%, preferably from 15 to 5% of the trans-isomer (VIII), suitable salts of the crystalline free base (IX) can be prepared. All salts are conceivable. In particular, these salts can be prepared by treating the compound of formula (IX) and, thus, the compound of formula (VII), with at least one suitable inorganic acid and/or at least one suitable organic acid, preferably at least one suitable inorganic Bronstedt acid and/or at least one suitable organic Bronstedt acid, optionally in at least one suitable solvent. Such suitable organic acids include, but are not limited to fumaric acid, oxalic acid, and tartaric acid. The suitable inorganic acids include, but are not limited to hydrochloric acid.

Therefore, the present invention also relates to the process as defined above, which further comprises (8) converting the compound of formula (IX), in particular the compound of formula (VII) and the compound of formula (VIII), to the respective salt by treating the compound with an inorganic or organic Bronstedt acid in a suitable solvent and preferably at least partially crystallizing the respective salt.

Among other, the fumaric acid salt or the oxalic acid or the tartaric acid salt or the hydrochloric acid salt of compound (IX) is preferred. The hydrochloric acid salt is even more preferred.

Suitable solvents according to the present invention are polar solvents. More preferably, the solvent is an ester such as ethyl acetate or isopropyl acetate, an ether such as dioxane, tetrahydrofuran or methyl tetrahydrofuran, a ketone such as acetone or methyl isobutyl ketone, a halogenated solvent such as dichloromethane, toluene, or a mixture of two or more of these solvents, more preferably a ketone is used as solvent. Most preferably the solvent is acetone.

Generally, such crystallization can be carried out according to any suitable method. Among others, cooling, addition of an antisolvent, solvent distillation, or a combination of two or more of these methods may be mentioned.

According to a preferred embodiment, this crystallization is carried out by adding a suitable antisolvent together with the acid or after the addition of the acid. Generally, every conceivable antisolvent can be employed provided that this antisolvent allows for reducing the solubility of the dissolved acid addition salt of compound of formula (IX) and thus also of formula (VII) to such an extent that the acid addition salt of compound (IX) and thus also of compound (VII) is at least partially crystallized. Preferably, the antisolvent is an ether such as MTBE or a saturated or unsaturated hydrocarbon such as cyclohexane, hexane, or heptane. More preferably the antisolvent is MTBE.

According to another preferred embodiment of the present invention, the compound of formula (IX) and thus also of formula (VII) as obtained from step (6.2) is directly converted into a suitable salt as herein described, namely by applying the salt formation and preferably also the at least partial crystallization described in step (8) without applying the crystallization of step (7). Optionally, a solvent change is performed after (6.2) prior to the salt formation.

Also in this embodiment of the present invention wherein step (7) is not performed, the fumaric acid salt or the oxalic acid salt or the tartaric acid salt or the hydrochloric acid salt of compound (IX) is preferred. The hydrochloric acid salt is even more preferred. Suitable solvents according to the present invention are polar solvents. More preferably, the solvent is an ester such as ethyl acetate or isopropyl acetate, an ether such as dioxane, tetrahydrofuran or methyl tetrahydrofuran, a ketone such as acetone or methyl isobutyl ketone, a halogenated solvent such as dichloromethane, toluene, or a mixture of two or more of these solvents, more preferably a ketone is used as solvent. Most preferably the solvent is acetone. Generally, such crystallization can be carried out according to any suitable method. Among others, cooling, addition of an antisolvent, solvent distillation, or a combination of two or more of these methods may be mentioned. According to a preferred embodiment, this crystallization is carried out by adding a suitable antisolvent together with the acid or after the addition of the acid. Generally, every conceivable antisolvent can be employed provided that this antisolvent allows for reducing the solubility of the dissolved acid addition salt of compound of formular (IX) to such an extent that the acid addition salt of compound (IX) is at least partially crystallized. Preferably, the antisolvent is an ether such as MTBE or a saturated or unsaturated hydrocarbon such as cyclohexane, hexane, or heptane. More preferably the antisolvent is MTBE.

Thus, the present invention also relates to a crystalline hydrochloric acid salt of a chiral compound of formula (IX)

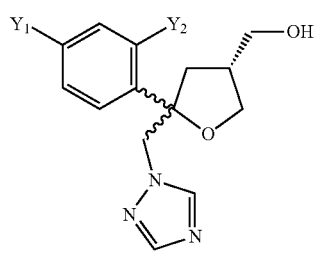

(IX)

wherein $Y_1$ and $Y_2$ are independently F or Cl, preferably F, and wherein from 80 to 95%, preferably from 85 to 95% of the molecules of said crystalline compound or the hydrochloride acid salt thereof are present as cis-isomer of formula (VII)

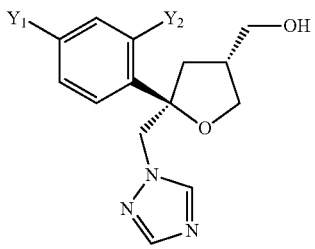

(VII)

and from 20 to 5%, preferably from 15 to 5% of the molecules of said crystalline compound or the hydrochlorid acid salt thereof are present as trans-isomer of formula (VII)

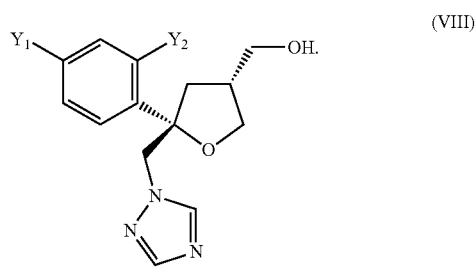

(VIII)

The crystalline hydrochloric acid salt of chiral compound of formula (IX) as herein described, wherein $Y_1$ and $Y_2$ are F, preferably exhibits the following X-ray diffraction pattern comprising at least the following reflections:

| Diffraction angle °2 Theta [Cu K(alpha 1)] | Relative Intensity (%) |
|---|---|
| 11.08 | 26 |
| 16.26 | 30 |
| 17.15 | 22 |
| 17.69 | 51 |
| 19.19 | 17 |
| 20.29 | 15 |
| 21.00 | 49 |
| 21.44 | 42 |
| 22.56 | 100 |
| 24.29 | 43 |
| 24.66 | 32 |
| 27.14 | 34 |
| 27.56 | 57 | wherein 100% relates to the intensity of the maximum peak in the X-ray diffraction pattern.

Further, the present invention relates to a preferably at least partially crystalline chiral compound or a salt thereof which is obtainable or obtained by a process as defined above, the process preferably comprising steps (1) to (8), even more preferably comprising steps (1) to (6.2) followed by (8).

As already mentioned above, the compound of formula (IX) or a salt thereof is preferably used as key compound for the preparation of an antifungal agent. The preferred antifungal agent for the preparation of which the compound of formula (IX) or a salt thereof and thus compound (VII) or a salt thereof can be employed is posaconazole, i.e. the compound according to the following formula:

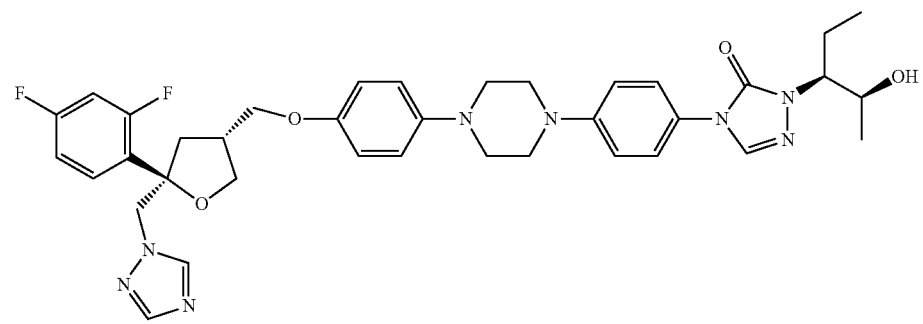 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

Thus, the present invention also relates to a method for the preparation of an antifungal agent, preferably posaconazole, wherein the preferably at least partially crystalline, preferably crystalline compound of formula (IX) or a salt thereof and thus (VII) or a salt thereof is employed as starting material.

According to an optional embodiment of the present invention, the compound of formula (IX) or the salt thereof can be suitably purified with respect to the cis-isomer (VII) or the trans-isomer (VIII), preferably the cis-isomer (VII), prior to its use for the preparation of an antifungal agent, preferably posaconazole.

The present invention is illustrated by the following examples.

EXAMPLES

Example 1

Preparation of the Compound of Formula (IX)

(a) Preparation of the Compound of Formula (IIa)

In 20 ml of MTBE, 3.8 g of Mg were suspended. The temperature of the suspension was 55° C. Then, 0.5 g of Grignard reagent $(CH_3)_3Si$—$CH_2MgCl$ in MTBE from a previous batch were added in order to dry the system (if no such Grignard reagent is available for the first batch, $(CH_3)_3Si$—$CH_2MgCl$ in diethyl ether (CAS Registry Number: 13170-43-9) commercially available as 1.0 M solution from Sigma-Aldrich can be used), followed by 1.0 ml of chloromethyl trimethyl silane (CM-TMS; CAS Registry Number: 2344-80-1; commercially available from Sigma-Aldrich). A solution of 14 ml of the CM-TMS in 43 ml of MTBE was added slowly over a period of 2 hours at a temperature of 55° C. The mixture was stirred for 2 hours at 55° C. and then cooled to a temperature of −10° C. Subsequently, 10.0 g of the commercial compound of formula (Ia) (CAS Registry Number: 51336-94-8; commercially available from Sigma-Aldrich) in 30 ml of MTBE were added and the temperature was kept in the range of from 0 to −10° C. The reaction mixture was quenched in a 20% (w/v) aqueous solution of ammonium chloride. The obtained organic layer was washed with a 20% (w/v) aqueous solution of ammonium chloride. The thus washed organic layer was then washed with water.

To the organic layer, 11.0 ml of concentrated sulphuric acid were added, and the temperature was kept at 25 to 30° C. Then, the reaction mixture was stirred at a temperature of from 45 to 50° C. for 3 hours. Subsequently, the reaction mixture was cooled to 20° C. and 25 ml of water were added, and the organic layer was separated. The obtained organic layer was extracted with an 9% (w/v) aqueous solution of sodium bicarbonate, followed by washing with water. The solvents of the washed organic layer were removed by distillation under reduced pressure, and the compound of formula (IIa) was obtained as an oil. The yield was 9.4 g, corresponding to a theoretical value of 95%.

(b) Preparation of the Compound of Formula (IIIa)

10.0 g of the compound of formula (IIa) (as oil, as obtained according to (a)) were dissolved in 20 ml of DMSO under stirring. Then, 3.2 g of NaOH flakes and 24.0 ml of diethyl malonate were added. The resulting suspension was stirred for 5 hours at 25 to 30° C. Subsequently, 100 ml of water were added, and the resulting mixture was stirred for 30 min. The thus obtained solution was extracted with 80 ml of cyclohexane at 25 to 30° C. After separation of the layers the aqueous layer was extracted with 40 ml of cyclohexane at 25 to 30° C. The combined organic layers were washed with a 5% (w/v) aqueous solution of NaOH, followed by washing with water. After washing, the solvents of the organic layer were removed by distillation under reduced pressure and the compound of formula (IIIa) was obtained as an oil. The yield was 15.0 g, corresponding to a theoretical value of 90.0%.

(c) Preparation of the Compound of Formula (IVa)

10.0 g of the compound of formula (IIIa) (as oil, as obtained according to (b)) were dissolved in 120 ml of isopropyl alcohol and 13.0 ml of water under stirring at 25 to 30° C. The resulting mixture was cooled to a temperature of from 0 to −5° C. Then, 2.3 g of lithium chloride and 2.1 g of sodium borohydride were added at 0 to −5° C. The resulting suspension was stirred at 25 to 30° C. for 20 hours. The pH of the stirred mixture was adjusted to a value of 1 (measured by using a calibrated pH meter) by addition of 4 N aqueous HCl. Afterwards, an 20% (w/v) aqueous solution of NaOH was added to adjust the pH to a value of 10 (measured by using a calibrated pH meter). The resulting mixture was stirred for 1 hour. Then, the lower aqueous layer was drained. From the separated organic layer, the isopropyl alcohol was distilled off, and an oil was obtained. To the oil, 100 ml of toluene and 100 ml of water were added, and the product was extracted into the toluene layer. The solvents of the resulting toluene layer were removed by distillation, under reduced pressure and the compound of formula (IVa) was obtained as oil. The yield was 6.0 g, corresponding to a theoretical value of 82.0%.

(d) Preparation of the Compound of Formula (Va)

10.0 g of the compound of formula (IVa) (as oil, as obtained according to (c)) were dissolved in 80 ml of toluene and cooled to −15° C. Then, 7.4 g of sodium bicarbonate, 0.5 g of enzyme (Novo SP 435; *Candida antarctica*, Novozym 435 from Novo Nordisk), and 7.9 ml of isobutyric anhydride were added. The resulting mixture was stirred at −15° C. for 24 hours. Then the solids were filtered off and the filtrate was washed with an 5% (w/v) aqueous solution of sodium bicarbonate, followed by washing with water. The solvents of the resulting organic layer were removed by distillation under reduced pressure to obtain the desired product as an oil. This oil was dissolved in 40 ml of n-heptane at 50 to 60° C. The clear solution was gradually cooled to a temperature of 10° C. The compound of formula (Va) crystallized as colorless crystals. The obtained solids were filtered, and the wet filter cake was washed with 20 ml of n-heptane. The filter cake was then dried at 40° C. in vacuo and the compound of formula (Va) was obtained as colorless crystals. The yield was 9.2 g, corresponding to a theoretical value of 70.0%.

(e) Preparation of the Compound of Formula (Xa)

10.0 g of the crystals obtained in (d) were dissolved in 80 ml of ethyl acetate under stirring. The resulting solution was cooled to −15° C., and 21.5 g of iodine and 7.0 g of sodium bicarbonate were added. The obtained suspension was stirred at −15° C. for 5 hours. The reaction mixture was quenched in 200 ml of a 10% (w/v) aqueous solution of sodium sulphite. The organic layer was washed with 100 ml of a 10% (w/v) aqueous solution of sodium sulphite, followed by washing with water. The solvents of the thus obtained, washed organic layer were removed by distillation under reduced pressure to obtain the compound of formula (Xa) as an oil. The yield was 13.5 g, corresponding to a theoretical value of 95.0%.

(f) Preparation of the Compound of Formula (IXa)

10.0 g of the compound of formula (Xa) (as oil, as obtained according to (e)) were dissolved in 80 ml of DMSO under stirring. Then, 10 g of the sodium salt of 1,2,4-triazole were added at 25 to 30° C., and the resulting reaction mixture was stirred for 24 hours at 85 to 90° C. The mixture was then cooled to 25 to 30° C., and 25 ml of 5% (w/v) aqueous solution of sodium hydroxide were added. The mixture was then stirred for 3 hours at 25 to 30° C. 100 ml of water were added, and the product was extracted into 150 ml of methyl tetrahydrofuran. The thus obtained organic layer was washed with a 10% (w/v) aqueous solution of sodium chloride, and subsequently the solvents of the resulting organic layer were removed by distillation under reduced pressure to obtain the compound of formula (IXa) as a crude oil. The yield was 6.0 g, corresponding to a theoretical value of 86.0%.

10.0 g of the crude oil were dissolved in 100 ml of methyl tetrahydrofuran under stirring at 50 to 60° C. Then, 300 ml of n-heptane were added at 50 to 60° C. over a period of 30 min. The turbid solution was cooled to 25 to 30° C. and stirred for another 30 min. The resulting suspension was cooled to 0 to −5° C. and stirred for 2 hours. The product was filtered, and the wet cake was washed with 20 ml of n-heptane. The washed product was dried at 40° C. in vacuo to obtain the crystalline compound of formula (IXa) as a colorless solid. The yield was 7.0 g, corresponding to a theoretical value of 70.0%.

The compound of formula (IXa) was obtained as mixture of the cis-isomer with the respective trans-isomer with a cis:trans ratio of 9:1.

Example 2

Preparation of Salts of the Compound of Formula (IX)

(a) Preparation of a Hydrochloride Salt 10.0 g of the compound of formula (IXa) as crude oil as obtained in Example 1 (f) prior to the crystallization were dissolved in 200 ml of acetone under stirring at 30 to 40° C. The resulting solution was cooled to 25 to 30° C. Then, HCl in MTBE (10 wt.-%) was added over a period of 15 min at 25 to 30° C. The solid crystallized when the mixture was stirred for 15 min. Then, 200 ml of MTBE were added slowly over a period of 30 min. The suspension was cooled to 0 to −5° C. and stirred for 2 hours. The product was filtered, and the wet cake was washed with 20 ml of MTBE. After drying at 70° C. in vacuo, the HCl salt of the compound (IXa) was obtained as colourless solid. The yield was 9.5 g, corresponding to a theoretical value of 85.0%.

The HCl salt of compound of formula (IXa) was obtained as mixture of the cis-isomer with the respective trans-isomer with a cis:trans ratio of 9:1.

(b) Preparation of Organic Acid Salts 10.0 g of the crystalline compound of formula (IXa) as obtained in Example 1 (f) above (cis:trans ratio=9:1) were dissolved in 20 ml of acetone. To the resulting solution, 1.1 molar equivalents of organic acid (oxalic acid, DL-tartaric acid, fumaric acid) were added at ambient temperature of from 25 to 30° C. The resulting mixtures were stirred for 1 hour at 25 to 30° C. Then, 150 ml of MTBE were added via a dropping funnel over a period of 15 min. The solids crystallized. Stirring was continued at 25 to 30° C. for 2 hours. The solids were isolated by filtration, washed with 20 ml of MTBE, and dried in vacuo at 45° C. The salts were obtained as colourless solids.

The following cis:trans ratios were obtained:

| organic salt | melting point/° C. | cis:trans[1] | % purity[1] |
|---|---|---|---|
| fumarate | 267 | >92:8 | >98% |
| oxalate | 120 | 90:10 | >98% |
| tartrate | 204 | >93:7 | >98% |

[1]determined via HPLC

HPLC Method for determination of purity and cis/trans ratio of compound of formula (IXa):

| Principle | Determination by HPLC using UV detector | |
|---|---|---|
| Reagents and Equipment | Potassium dihydrogen phosphate | Merck Cat. No. 60487305001730 |
| | Orthophosphoric acid (85%) | AR Grade e.g (Merck, Cat. No. 61768205001046) |
| | Acetonitrile | HPLC grade (e.g. Merck Cat. No. 61830025001046) |
| | HPLC system | Agilent 1100 series or similar |
| | pH meter | e.g. Metrohm or equivalent |
| Buffer Preparation | Dissolve 2.72 g of Potassium dihydrogen phosphate in 1000 ml of water and adjust the pH to 3.0 ± 0.05 by adding dilute orthophosphoric acid (85%) using a pH meter. Filter through 0.45 μm (micrometer) filter and degas. | |
| Diluent | Buffer:Methanol (80:20) v/v | |
| Chromatographic Conditions | | |
| Column | $C_{16}$, 250 mm × 4.6 mm i.d. 5μ, e.g. Ascentis RP amide or equivalent column can be used after appropriate validation. | |
| System | Gradient | |
| Column Temperature | 40° C. | |
| Mobile phase A | Buffer | |
| Mobile phase B | Buffer:Acetonitrile (30:70) v/v | |
| Flow rate | 2.0 ml/min | |
| Injection temperature | 25° C. | |
| Injection volume | 25 μl (microliter) | |
| Run time | 45 minutes | |
| Detection wavelength | 210 nm | |
| System | Gradient | |
| | Time | % mobile phase B |
| Gradient program | 0 | 20 |
| | 5 | 20 |
| | 15 | 40 |
| | 25 | 80 |
| | 28 | 90 |
| | 39 | 90 |
| | 41 | 20 |
| | 45 | 20 |

Method for the Recording of X-Ray Diffractograms

The samples were analysed on the Zero background holder in spinning mode at ambient conditions. A typical precision of the 2-Theta values is in the range of about ±0.2° 2-Theta. Thus a diffraction peak that appears at 8.6° 2-Theta can appear between 8.4 and 8.8° 2-Theta on most X-ray diffractometers under standard conditions.

Instrument Parameters:

XRD Measurement Conditions:

| Instrument | X'PERT PRO PANalytical |
|---|---|
| Scan Axis | Gonio |
| Start Position [°2Th.] | 3.0 |
| End Position [°2Th.] | 40.0 |
| Step Size [°] | 0.0170 |
| Scan Step Time [s] | 100 |
| Scan Type | Continuous |
| Anode Material | Cu |
| Generator Settings | 45 kV, 40 mA |
| Spinning | Yes |

Incident Beam Optics

| Soller Slits | 0.02 radians |
| --- | --- |
| Divergence Slit Type | Programmable Slits (Fixed 0.5°) |
| AntiScatter Slits | Fixed Slits (1°) |
| Beam Mask | 10 mm (MPD/MRD) |

Diffracted Beam Optics

| Antiscatter Slit | Programmable Slits (Fixed 0.5°) |
| --- | --- |
| Soller Slits | 0.02 radians |
| Filter | Nickel |
| Detector | X'celerator |
| Mode | Scanning |
| Active Path Length | 2.122° |

LIST OF CITED DOCUMENTS

WO 94/25452 A1
WO 95/16658 A1
D. J. Peterson, Carbonyl olefination reaction using silyl-substituted organometallic compounds; J. Org. Chem. (1968) 33 (2) pp. 780-784
P. Blundell et al., Synlett 1994, pp. 263-265
Tetrahedron Letters 32 (1991), pp. 7545-7548
WO 97/22710 A1

The invention claimed is:

1. A crystalline chiral compound of formula (IX) or a salt thereof

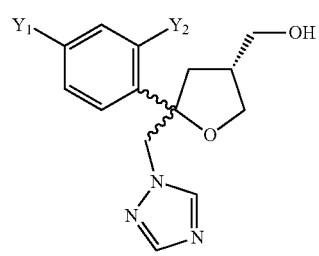

wherein $Y_1$ and $Y_2$ are independently F or Cl and wherein from 80 to 95% of the molecules of said crystalline compound or the salt thereof are present as cis-isomer of formula (VII) or the salt thereof

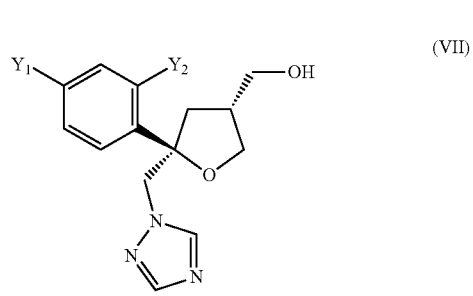

and from 20 to 5% of the molecules of said crystalline compound or the salt thereof are present as trans-isomer of formula (VIII) or the salt thereof

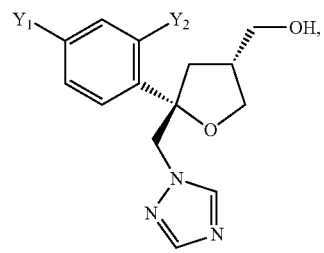

wherein $Y_1$ and $Y_2$ are F having an X-ray diffraction pattern comprising at least the following reflections:

| Diffraction angle °2 Theta [Cu K(alpha 1)] | Relative Intensity (%) |
| --- | --- |
| 7.05 | 19 |
| 8.03 | 51 |
| 9.25 | 20 |
| 11.92 | 24 |
| 13.79 | 36 |
| 15.88 | 25 |
| 16.65 | 100 |
| 20.15 | 42 |
| 21.37 | 45 |
| 22.04 | 37 |
| 24.04 | 96 |
| 27.80 | 20 | wherein 100% relates to the intensity of the maximum peak in the X-ray diffraction pattern.

2. The crystalline chiral compound according to claim 1, wherein $Y_1$ and $Y_2$ are F.

3. The crystalline chiral compound according to claim 1, wherein from wherein from 85 to 95% of the molecules of said crystalline compound or the salt thereof are present as cis-isomer of formula (VII) or the salt thereof.

4. The crystalline chiral compound according to claim 1, wherein from 15 to 5% of the molecules of said crystalline compound or the salt thereof are present as trans-isomer of formula (VIII) or the salt thereof.

* * * * *